US009187556B2

(12) United States Patent
Tsunoda et al.

(10) Patent No.: US 9,187,556 B2
(45) Date of Patent: Nov. 17, 2015

(54) SEMA5B PEPTIDES AND VACCINES INCLUDING THE SAME

(75) Inventors: Takuya Tsunoda, Kanagawa (JP); Ryuji Osawa, Kanagawa (JP); Sachiko Yoshimura, Kanagawa (JP); Tomohisa Watanabe, Kanagawa (JP); Gaku Nakayama, Kanagawa (JP); Yusuke Nakamura, Tokyo (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 14/118,693

(22) PCT Filed: Jun. 7, 2012

(86) PCT No.: PCT/JP2012/003740
§ 371 (c)(1),
(2), (4) Date: Feb. 28, 2014

(87) PCT Pub. No.: WO2012/169200
PCT Pub. Date: Dec. 13, 2012

(65) Prior Publication Data
US 2014/0178409 A1 Jun. 26, 2014

Related U.S. Application Data

(60) Provisional application No. 61/495,819, filed on Jun. 10, 2011.

(51) Int. Cl.
| C07K 14/00 | (2006.01) |
| C07K 16/18 | (2006.01) |
| C07K 14/47 | (2006.01) |
| G01N 33/574 | (2006.01) |
| A61K 39/00 | (2006.01) |
| A61K 38/00 | (2006.01) |

(52) U.S. Cl.
CPC ............. *C07K 16/18* (2013.01); *A61K 39/0011* (2013.01); *C07K 14/4703* (2013.01); *G01N 33/57492* (2013.01); *A61K 38/00* (2013.01); *G01N 2333/70539* (2013.01)

(58) Field of Classification Search
None
See application file for complete search history.

(56) References Cited

U.S. PATENT DOCUMENTS

| 7,875,424 | B2 | 1/2011 | Türeci et al. |
| 8,629,097 | B2 * | 1/2014 | Jo et al. ........................... 514/1.2 |
| 2003/0109434 | A1 | 6/2003 | Algate et al. |
| 2007/0248628 | A1 | 10/2007 | Keller et al. |
| 2008/0166340 | A1 | 7/2008 | Tureci et al. |
| 2009/0214550 | A1 | 8/2009 | Sahin et al. |

FOREIGN PATENT DOCUMENTS

| CN | 101278059 A | 10/2008 |
| WO | WO 02/74237 A2 | 9/2002 |
| WO | WO 2005/030250 A2 | 4/2005 |
| WO | WO 2006/100089 A2 | 9/2006 |
| WO | WO 2007/013575 A2 | 2/2007 |
| WO | 2008093982 * | 8/2008 |

OTHER PUBLICATIONS

Ezzell (J. NIH Res. 1995 7:46).*
Spitler (Cancer Biotherapy, 1995, 10:1-3).*
Boon (Adv. Can. Res. 1992 58:177-210).*
Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Boon, "Tumor Antigens Recognized by Cytolytic T Lymphocytes: Present Perspectives for Specific Immunotherapy", *Int. J. Cancer*, 1993, vol. 54, pp. 177-180.
Boon et al., "Human Tumor Antigens Recognized by T Lymphocytes", *J. Exp. Med.*, 1996, vol. 183, pp. 725-729.
Harris, "Structure and Function of the p53 Tumor Suppressor Gene: Clues for Rational Cancer Therapeutic Strategies", *J. Natl. Cancer Inst.*, 1996, vol. 88, No. 20, pp. 1442-1455.
Butterfield et al., "Generation of Human T-cell Responses to an HLA-A2.1- restricted Peptide Epitope Derived from α-Fetoprotein", *Cancer Res.*, 1999, vol. 59, pp. 3134-3142.
Vissers et al., "The Renal Cell Carcinoma-associated Antigen G250 Encodes a Human Leukocyte Antigen (HLA)-A2.1-restricted Epitope Recognized by Cytotoxic T Lymphocytes", *Cancer Res.*, 1999, vol. 59, pp. 5554-5559.
Van Der Burg et al., "Immunogenicity of Peptides Bound to MHC Class I Molecules Depends on the MHC-Peptide Complex Stability", 1996, *J. Immunol.*, vol. 156, No. 9, pp. 3308-3314.
Tanaka et al., "Induction of Antitumor Cytotoxic T Lymphocytes with a MAGE-3-encoded Synthetic peptide Presented by Human Leukocytes Antigen-A24", *Cancer Res.*, 1997, vol. 57, pp. 4465-4468.

(Continued)

*Primary Examiner* — Sheela J Huff
(74) *Attorney, Agent, or Firm* — Kilpatrick Townsend & Stockton LLP

(57) ABSTRACT

As discussed in detail herein, isolated epitope peptides derived from SEMA5B bind to an HLA antigen and induce cytotoxic T lymphocytes (CTL) and thus are suitable for use in the context of cancer immunotherapy, more particularly cancer vaccines. The inventive peptides encompass both the above mentioned amino acid sequences and modified versions thereof, in which one, two, or several amino acids are substituted, deleted, inserted or added, provided such modified versions retain the requisite HLA binding and/or CTL inducibility of the original sequences. Further provided are polynucleotides encoding any of the aforementioned peptides as well pharmaceutical agents or compositions that include any of the aforementioned peptides or polynucleotides. The peptides, polynucleotides, pharmaceutical agents or compositions of this invention find particular utility in the treatment and/or prevention of cancers and tumors, including, for example, esophageal cancer, NSCLC, RCC and SCLC.

7 Claims, 2 Drawing Sheets

(56) References Cited

OTHER PUBLICATIONS

Fujie et al., "A Mage-1-encoded HLA-A24-binding Specific Antitumor Cytotoxic T Lymphocytes", *Int. J. Cancer*, 1999, vol. 80, pp. 169-172.
Kikuchi et al., "Identification of a Sart-1-derived peptide Capable of Inducing HLA-A24-restricted and Tumor-specific Cytotoxic T Lymphocytes", *Int. J. Cancer*, 1999, vol. 81, pp. 459-466.
Oiso et al., "A Newly Identified Mage-3-derived Epitope Recognized by HLA-A24-restricted Cytotoxic T Lymphocytes", *Int. J. Cancer*, 1999, vol. 81, pp. 387-394.
Belli et al., "Vaccination of Metastatic Melanoma Patients with Autologous Tumor-Derived Heat Shock Protein gp96-Peptide: Clinical and Immunologic Findings", *J. Clin. Oncol.*, 2002, vol. 20, No. 20, pp. 4169-4180.
Coulie et al., "Cytolytic T-cell Responses of Cancer Patients Vaccinated with a Mage antigen", *Immunol. Rev.*, 2002, vol. 188, pp. 33-42.
Rosenberg et al., "Cancer Immunotherapy: Moving Beyond Current Vaccines", *Nat. Med.*, 2004, vol. 10, No. 9, pp. 909-915.
O'Connor et al., "Semaphorin 5B Mediates Synapse Elimination in Hippocampal Neurons", *Neural Dev.*, 2009, 4:18, 19 pages.
Hirota et al., "Genome-wide Gene Expression Profiles of Clear Cell Renal Cell Carcinoma: Identification of Molecular Targets for Treatment of Renal Cell Caarcinoma", *Int. J. Oncol.*, 2006, vol. 29, pp. 799-827.
Nakamura et al., "Method for Diagnosing and Treating Renal Cell Carcinoma", U.S. Appl. No. 11/913,147, filed Oct. 30, 2007, 119 pages.
Kondo et al., "Prominent Roles of Secondary Anchor Residues in Peptide Binding to HLA-A24 Human Class I Molecules", *J. Immunol.*, 1995, vol. 155, pp. 4307-4312.
Kubo et al., "Definition of Specific Peptide Motifs for Four Major HLA-A Alleles", *J. Immunol.*, 1994, vol. 152, pp. 3913-3924.
Adams et al., "Prediction of Binding to MHC Class I Molecules" *J. Immunol. Methods*, 1995, vol. 185, pp. 181-190.
Schueler-Furman et al., "Structure-based Prediction of Binding Peptides to MHC Class I Molecules: Application to a Broad Range of MHC Alleles", *Protein Sci.*, 2000, vol. 9, pp. 1838-1846.
Zaremba et al., "Identification of an Enhancer Agonist Cytotoxi T Lymphocyte Peptide from Human Carcinoembryonic Antigen", *Cancer Res.*, 1997, vol. 57, pp. 4570-4577.
Falk et al., "Allele-specific Motifs Revealed by Sequencing of Self-peptides Eluted from MHC Molecules", Nature, 1991, vol. 351, pp. 290-296.
Hoffmann et al., "The Ability of Variant peptides to Reverse the Nonresponsiveness of T Lymphocytes to the Wild-Type Sequence p. 53 264-272 Epitope", J. Immunol., 2002, vol. 168, pp. 1338-1347.
Dionne et al., "Functional Characterization of CTL Against gp100 Altered Peptide Ligands", *Cancer Immunol. Immunother.*, 2003, vol. 52, pp. 199-206.
Dionne et al., "Her-2/neu Altered Peptide Ligand-induced CTL Responses: Implicatons for Petptides with Increased HLA Affinity and T-cell-receptor Interaction", *Cancer Immunol. Immunother.*, 2004, vol. 53, pp. 307-314.
Rammensee et al., "MHC Ligands and Peptide Motifs: First Listing", *Immunogenetics*, 1995, vol. 41, pp. 178-228.
Parker et al., "Scheme for Ranking Potential HLA-A2 Binding Peptides Based on Independent Peptide Side-Chains", *J. Immunol.*, 1994, vol. 152, pp. 163-175.
Stevanovic, "Identification of Tumour-Associated T-Cell Epitopes for Vaccine Development", *Nat Rev Cancer*, 2(7):514-520 (2002).
PCT International Search Report and Written Opinion for PCT/JP2012/003740, mailed Sep. 4, 2012, 13 pgs.
U.S. Appl. No. 14/648,433, filed May 29, 2015, 118 pages.

\* cited by examiner

SEMA5B PEPTIDES AND VACCINES INCLUDING THE SAME

PRIORITY

The present application is a U.S. National Phase of PCT/JP2012/003740, filed Jun. 7, 2012, which claims the benefit of U.S. Provisional Application No. 61/495,819, filed on Jun. 10, 2011, the entire contents of which are incorporated by reference herein in their entirety.

REFERENCE TO SEQUENCE LISTING

This application includes a Sequence Listing as a text file named "87331-026710US-891476.txt" created Nov. 18, 2013, and containing 40,123 bytes. The material contained in this text file is incorporated by reference in its entirety for all purposes.

TECHNICAL FIELD

The present invention relates to the field of biological science, more specifically to the field of cancer therapy. In particular, the present invention relates to novel peptides that are effective as cancer vaccines, as well as drugs for either or both of treating and preventing tumors.

BACKGROUND ART

It has been demonstrated that cytotoxic T lymphocytes (CTLs) recognize epitope peptides derived from tumor-associated antigens (TAAs) found on major the histocompatibility complex (MHC) class I molecule, and then kill the tumor cells. Since the discovery of melanoma antigen (MAGE) family as the first example of TAAs, many other TAAs have been discovered through immunological approaches (NPL 1, Boon T, Int J Cancer 1993 May 8, 54(2): 177-80; NPL 2, Boon T & van der Bruggen P, J Exp Med 1996 Mar. 1, 183(3): 725-9). Some of these TAAs are currently undergoing clinical development as immunotherapeutic targets.

Favorable TAAs are indispensable for the proliferation and survival of cancer cells. The use of such TAAs as targets for immunotherapy may minimize the well-described risk of immune escape of cancer cells attributable to deletion, mutation, or down-regulation of TAAs as a consequence of therapeutically driven immune selection. Accordingly, the identification of new TAAs capable of inducing potent and specific anti-tumor immune responses, warrants further development; accordingly, the clinical application of peptide vaccination strategies for various types of cancer is ongoing (NPL 3, Harris C C, J Natl Cancer Inst 1996 Oct. 16, 88(20): 1442-55; NPL 4, Butterfield L H et al., Cancer Res 1999 Jul. 1, 59(13): 3134-42; NPL 5, Vissers J L et al., Cancer Res 1999 Nov. 1, 59(21): 5554-9; NPL 6, van der Burg S H et al., J Immunol 1996 May 1, 156(9): 3308-14; NPL 7, Tanaka F et al., Cancer Res 1997 Oct. 15, 57(20): 4465-8; NPL 8, Fujie T et al., Int J Cancer 1999 Jan. 18, 80(2): 169-72; NPL 9, Kikuchi M et al., Int J Cancer 1999 May 5, 81(3): 459-66; NPL 10, Oiso M et al., Int J Cancer 1999 May 5, 81(3): 387-94). To date, several clinical trials using these tumor-associated antigen derived peptides have been reported. Unfortunately, many of the current cancer vaccine trial have shown only a low objective response rate (NPL 11, Belli F et al., J Clin Oncol 2002 Oct. 15, 20(20): 4169-80; NPL 12, Coulie P G et al., Immunol Rev 2002 October, 188: 33-42; NPL 13, Rosenberg S A et al., Nat Med 2004 September, 10(9): 909-15). Accordingly, there remains a need for new TAAs as immunotherapeutic targets.

SEMA5B is a member of the semaphorin protein family, a family of proteins that play an important role in axonal guidance during neural development (NPL 14, O'Connor T P et. al., Neural Dev. 2009 May 23; 4:18). Recent studies suggest that the functions of semaphorin family protein relate not only to nervous system but to organogenesis, angiogenesis and a development of cancer.

In the course of gene-expression profile analyses using a cDNA microarray consisting of 23,040 genes as a means to clarify the molecular mechanism of renal cell carcinoma (RCC), SEMA5B was found to be frequently up-regulated in RCC. Subsequent Northern blot analysis reveals that SEMA5B transcript is highly expressed in RCC tissues but barely detectable in normal human tissues except fetal brain and fetal kidney. Furthermore, knockdowns of SEMA5B by siRNA in RCC cell lines have been shown to attenuate the growth of RCC cells (NPL15, Hirota E. et. al., Int J. Oncol. 2006 October; 29(4):799-827; PTL1, WO2007/013575).

CITATION LIST

Patent Literature

[PTL1] WO2007/013575

Non Patent Literature

[NPL 1] Boon T, Int J Cancer 1993 May 8, 54(2): 177-80
[NPL 2] Boon T & van der Bruggen P, J Exp Med 1996 Mar. 1, 183(3): 725-9
[NPL 3] Harris C C, J Natl Cancer Inst 1996 Oct. 16, 88(20): 1442-55
[NPL 4] Butterfield L H et al., Cancer Res 1999 Jul. 1, 59(13): 3134-42
[NPL 5] Vissers J L et al., Cancer Res 1999 Nov. 1, 59(21): 5554-9
[NPL 6] van der Burg S H et al., J Immunol 1996 May 1, 156(9): 3308-14
[NPL 7] Tanaka F et al., Cancer Res 1997 Oct. 15, 57(20): 4465-8
[NPL 8] Fujie T et al., Int J Cancer 1999 Jan. 18, 80(2): 169-72
[NPL 9] Kikuchi M et al., Int J Cancer 1999 May 5, 81(3): 459-66
[NPL 10] Oiso M et al., Int J Cancer 1999 May 5, 81(3): 387-94
[NPL 11] Belli F et al., J Clin Oncol 2002 Oct. 15, 20(20): 4169-80
[NPL 12] Coulie P G et al., Immunol Rev 2002 October, 188: 33-42
[NPL 13] Rosenberg S A et al., Nat Med 2004 September, 10(9): 909-15
[NPL 14] O'Connor T P et. al., Neural Dev. 2009 May 23; 4:18
[NPL 15] Hirota E. et. al., Int J. Oncol. 2006 October; 29(4):799-827

SUMMARY OF INVENTION

The present invention is based, at least in part, on the discovery of novel peptides that may serve as suitable targets of immunotherapy. Because TAAs are generally perceived by the immune system as "self" and therefore often have no immunogenicity, the discovery of appropriate targets is of extremely importance. As noted above, SEMA5B (for example, SEQ ID NO: 49 encoded by the gene of GenBank Accession No. NM_001031702 (SEQ ID NO: 48)) has been identified as up-regulated in cancers, examples of which include, but are not limited to, esophageal cancer, non-small cell lung cancer (NSCLC), RCC and small cell lung cancer (SCLC). Thus, the present invention focuses on SEMA5B as a candidate target of cancer/tumor immunotherapy, more particularly novel SEMA5B epitope peptides that may serve as suitable immunotherapeutic targets.

To that end, the present invention is directed, at least in part, to the identification of specific epitope peptides that possess the ability to induce CTLs specific to SEMA5B among peptides derived from SEMA5B. As discussed in greater detail below, peripheral blood mononuclear cells (PBMCs) obtained from a healthy donor were stimulated using HLA-A*0201 binding candidate peptides derived from SEMA5B. CTL lines were then established with specific cytotoxicity against the HLA-A2 positive target cells pulsed with each of candidate peptides. The results herein demonstrate that these peptides are HLA-A2 restricted epitope peptides that may induce potent and specific immune responses against cells expressing SEMA5B. These results further indicate that SEMA5B is strongly immunogenic and the epitopes thereof are effective targets for cancer/tumor immunotherapy.

Accordingly, it is an object of the present invention to provide isolated peptides that bind to HLA antigen and include an immunologically active fragment of the SEMA5B (SEQ ID NO: 49). Such peptides are expected to have CTL inducibility and, thus, can be used to induce CTL in vitro or ex vivo or to be administered to a subject for inducing immune responses against cancers, examples of which include, but are not limited to esophageal cancer, NSCLC, RCC and SCLC. Preferred peptides are nonapeptides and decapeptides, more preferably, nonapeptides and decapeptides having an amino acid sequence selected from among SEQ ID NOs: 1 to 7 and 9 to 47. Peptides having an amino acid sequence selected from among SEQ ID NOs: 5, 7, 27 and 34 showed strong CTL inducibility and thus are particularly preferred.

The present invention also contemplates modified peptides having an amino acid sequence selected from among SEQ ID NOs: 5, 7, 27 and 34 in which one, two or more amino acids are substituted, deleted, inserted or added, so long as the modified peptides retain the requisite CTL inducibility of the original unmodified peptide. To that end, the present invention provides an isolated peptide of less than 14, 13, 12, 11, or 10 amino acids in length and comprising the amino acid sequence selected from the group consisting of:

(i) an amino acid sequence selected from the group consisting of SEQ ID NOs: 5 and 7, in which 1, 2, or several amino acid(s) are substituted, deleted, inserted or added, provided the resulting modified peptide binds an HLA antigen and induces a cytotoxic T lymphocyte, and (ii) the amino acid sequence of (i), wherein the amino acid sequence has one or both of the following characteristics:

(a) the second amino acid from the N-terminus of said SEQ ID NO is selected from the group consisting of leucine and methionine; and (b) the C-terminal amino acid of said SEQ ID NO is selected from the group consisting of valine and leucine.

The present invention also contemplates modified peptides of less than 15, 14, 13, 12, or 11 amino acids in length comprising the amino acid sequence selected from the group consisting of:

(i') an amino acid sequence selected from the group consisting of SEQ ID NOs: 27 and 34, in which 1, 2, or several amino acid(s) are substituted, deleted, inserted or added, provided the resulting modified peptide binds an HLA antigen and induces a cytotoxic T lymphocyte, and (ii') the amino acid sequence of (i'), wherein the amino acid sequence has one or both of the following characteristics:

(a) the second amino acid from the N-terminus of said SEQ ID NO is selected from the group consisting of leucine and methionine; and (b) the C-terminal amino acid of said SEQ ID NO is selected from the group consisting of valine and leucine.

As demonstrated herein, such peptides can be processed in an APC to present a peptide of (i), (ii), (i') or (ii') thereon, when these peptides are contacted with, or introduced in an APC.

Also, the present invention contemplates modified peptides having an amino acid sequence that one, two or more amino acids substitution, deletion, insertion and/or addition in the amino acid sequence selected from among SEQ ID NOs: 5, 7, 27 and 34, so long as the modified peptides retain the requisite CTL inducibility of the original peptide. To that end, the present invention provides an isolated peptide of less than 14, 13, 12, 11, or 10 amino acids in length comprising the amino acid sequence selected from the group consisting of:

(i) an amino acid sequence that 1, 2, or several amino acid(s) are substituted, deleted, inserted or added in the amino acid sequence selected from the group consisting of SEQ ID NOs: 5 and 7, wherein the peptide binds an HLA antigen and induces cytotoxic T lymphocytes, and (ii) the amino acid sequence of (i), wherein the amino acid sequence has one or both of the following characteristics:

(a) the second amino acid from the N-terminus of said SEQ ID NO is selected from the group consisting of leucine and methionine; and (b) the C-terminal amino acid of said SEQ ID NO is selected from the group consisting of valine and leucine.

Moreover, the present invention also provides an isolated peptide of less than 15, 14, 13, 12, or 11 amino acids in length comprising the amino acid sequence selected from the group consisting of:

(i') an amino acid sequence that 1, 2, or several amino acid(s) are substituted, deleted, inserted or added in the amino acid sequence selected from the group consisting of SEQ ID NOs: 27 and 34, wherein the peptide binds an HLA antigen and induces cytotoxic T lymphocytes, and (ii') the amino acid sequence of (i'), wherein the amino acid sequence has one or both of the following characteristics:

(a) the second amino acid from the N-terminus of said SEQ ID NO is selected from the group consisting of leucine and methionine; and (b) the C-terminal amino acid of said SEQ ID NO is selected from the group consisting of valine and leucine.

These peptides are processed in an APC to present a peptide of (i), (ii), (i'), or (ii') thereon, when these peptides are contacted with, or introduced in an APC.

The present invention further encompasses isolated polynucleotides that encode any of the peptides of the present invention. These polynucleotides can be used to induce or prepare APCs having CTL inducibility. Like the above-described peptides of the present invention, such APCs can be administered to a subject for inducing immune responses against cancers.

When administered to a subject, the peptides of the present invention are presented on the surface of APCs so as to induce CTLs targeting the respective peptides. Therefore, one object of the present invention is to provide agents or compositions that include or incorporate any peptides or polynucleotides provided by the present invention for inducing CTLs. Such agents or compositions can be used for the treatment and/or prophylaxis of cancer and/or the prevention of a postoperative recurrence thereof, especially cancers such as esophageal cancer, NSCLC, RCC and SCLC. Thus, it is yet another object of the present invention to provide pharmaceutical agents or compositions for the treatment and/or prophylaxis of cancer and/or the prevention of a postoperative recurrence thereof, such pharmaceuticals formulated to include one or more peptides or polynucleotides of the present invention. Instead of or in addition to the peptides or polynucleotides of the present invention, the pharmaceutical agents or compositions of the present invention may include as active ingredients APCs or exosomes that present any of the peptides of the present invention.

The peptides or polynucleotides of the present invention may be used to induce APCs that present on the surface a complex of an HLA antigen and a peptide of the present invention, for example, by contacting APCs derived from a subject with the peptide of the present invention or introducing a polynucleotide encoding a peptide of the present invention into APCs. Such APCs have the ability of inducing CTLs that specifically recognize cells that present target peptides on their surface and find use in cancer immunotherapy. Accordingly, the present invention encompasses the methods for inducing APCs having CTL inducibility as well as the APCs obtained by such methods. In addition, the present invention also encompasses the agents or compositions for inducing APCs having CTL inducibility, such agents or compositions including any peptides or polynucleotides of the present invention.

It is further object of the present invention to provide methods for inducing CTL, such methods including the step of co-culturing CD8 positive T cells with APCs or exosomes presenting the peptide of the present invention on its surface or the step of introducing a polynucleotide encoding both of T cell receptor (TCR) subunits or polynucleotides encoding each of TCR subunit, wherein the TCR can bind to a complex of the peptide of the present invention and an HLA antigen presented on cell surface. CTLs obtained by such methods can find use in the treatment and/or prevention of cancer, examples of which include, but are not limited to, esophageal cancer, NSCLC, RCC and SCLC.

Yet another object of the present invention is to provide isolated APCs that present on the surface a complex of an HLA antigen and a peptide of the present invention. The present invention further provides isolated CTLs that target peptides of the present invention. These APCs and CTLs may be used for cancer immunotherapy.

It is yet another object of the present invention to provide methods for inducing an immune response against a cancer in a subject in need thereof, such methods including the step of administering agents or compositions including at least one component selected from among the SEMA5B polypeptides or immunologically active fragments thereof, polynucleotides encoding thereof, exosomes or the APCs presenting thereof and CTLs that recognize cells presenting thereof on their surface.

The applicability of the present invention extends to any of a number of the diseases relating to or arising from SEMA5B over-expression, such as cancer, examples of which include, but are not limited to, cancers include esophageal cancer, NSCLC, RCC and SCLC.

More specifically, the present invention provides followings:

[1] An isolated peptide consisting of the amino acid sequence of SEQ ID NO: 49 or an immunologically active fragment thereof, wherein said peptide binds an HLA antigen and induces cytotoxic T lymphocytes (CTLs),

[2] The isolated peptide of [1], wherein the HLA antigen is HLA-A2,

[3] The isolated peptide of [1] or [2], wherein said peptide comprises an amino acid sequence selected from the group consisting of SEQ ID NOs: 5, 7, 27 and 34,

[4] An isolated peptide selected from the group consisting of:
(a) an isolated peptide that binds to an HLA antigen and induces cytotoxic T lymphocytes (CTLs), and which comprises an immunologically active fragment of the peptide consisting of the amino acid sequence of SEQ ID NO: 49,
(b) the isolated peptide of (a), which comprises an amino acid sequence selected from the group consisting of SEQ ID NOs: 5, 7, 27 and 34,
(c) an isolated peptide that (i) comprises an amino acid sequence in which 1, 2, or several amino acid(s) are substituted, deleted, inserted, and/or added in the amino acid sequence of the peptide of (a) or (b), (ii) binds to an HLA antigen, and (iii) retains the CTL inducibility of the original peptide, and
(d) the isolated peptide of (a), (b) or (c), wherein the HLA antigen is HLA-A2,

[5] The isolated peptide of [4], wherein the isolated peptide has one or both of the following characteristics:
(a) the second amino acid from the N-terminus is selected from the group consisting of leucine and methionine; and
(b) the C-terminal amino acid is selected from the group consisting of valine and leucine,

[6] The isolated peptide of any one of [1] to [5], wherein said peptide is a nonapeptide or decapeptide,

[7] An isolated polynucleotide encoding the peptide of any one of [1] to [6],

[8] A composition for inducing CTL, wherein the composition comprises one or more peptide(s) of any one of [1] to [6], or one or more polynucleotide(s) of [7],

[9] A pharmaceutical composition, wherein the composition comprises at least one active ingredient selected from among,
(a) one or more peptide(s) of any one of [1] to [6];
(b) one or more polynucleotide(s) of [7];
(c) one or more exosome(s) or APC(s) presenting the peptide of any one of [1] to [6] on their surface;
(d) one or more CTL(s) that recognize(s) a cell presenting the peptide of any one of [1] to [6] on its surface; and
(e) combination thereof
formulated for a purpose selected from the group consisting of:
(i) the treatment of cancer,
(ii) the prophylaxis of cancer,
(iii) the prevention of a post-operative recurrence thereof, and
(iv) combinations thereof,

[10] The pharmaceutical composition of [9], wherein said composition is formulated for administration to a subject whose HLA antigen is HLA-A2,

[11] The pharmaceutical composition of [9] or [10], wherein said composition is formulated for the treatment of cancer,

[12] A method for inducing an antigen-presenting cell (APC) having CTL inducibility, said method comprising a step selected from the group consisting of:
(a) contacting an APC with the peptide of any one of [1] to [6] in vitro, ex vivo or in vivo, and
(b) introducing a polynucleotide encoding the peptide of any one of [1] to [6] into an APC,

[13] A method for inducing a CTL, said method comprising a step selected from the group consisting of:
(a) co-culturing a CD8 positive T cell with an APC that presents on its surface a complex of an HLA antigen and the peptide of any one of [1] to [6];
(b) co-culturing a CD8 positive T cell with an exosome that presents on its surface a complex of an HLA antigen and the peptide of any one of [1] to [6]; and
(c) introducing a polynucleotide encoding both of T cell receptor (TCR) subunits or polynucleotides encoding each of TCR subunits into a CD8 positive T cell, wherein the TCR can bind to a complex of an HLA antigen and the peptide of any one of [1] to [6] presented on a cell surface,

[14] An isolated APC that presents on its surface a complex of an HLA antigen and the peptide of any one of [1] to [6],

[15] The APC of [14], which is induced by the method of [12],

[16] An isolated CTL that targets the peptide of any one of [1] to [6],

[17] The CTL of [16], wherein said CTL is induced by the method of [13],

[18] A method of inducing an immune response against cancer in a subject in need thereof, said method comprising the step of administering to the subject a composition comprising a peptide of any one of [1] to [6], an immunologically active fragment thereof, or a polynucleotide encoding the peptide or the fragment,

[19] An antibody or immunologically active fragment thereof against the peptide of any one of [1] to [6],

[20] A vector comprising a nucleotide sequence encoding the peptide of any one of [1] to [6],

[21] A host cell transformed or transfected with an expression vector according to [20], and

[22] A diagnostic kit comprising the peptide of any one of [1] to [6], the polynucleotide of [7] or the antibody of [19].

In another embodiment, the isolated peptide of [4] may be selected from the group consisting of:
(a) an isolated peptide that binds to an HLA antigen and induces cytotoxic T lymphocytes (CTLs) and consists of the amino acid sequence of SEQ ID NO: 49 or an immunologically active fragment thereof,
(b) the isolated peptide of (a) or (b), which comprises an amino acid sequence selected from the group consisting of SEQ ID NOs: 5, 7, 27 and 34,
(c) an isolated peptide that comprises an amino acid sequence selected from the group consisting of SEQ ID NOs: 5, 7, 27 and 34, in which 1, 2, or several amino acid(s) are substituted, deleted, inserted, or added, provided said modified peptide binds to an HLA antigen and retains the CTL inducibility of the original peptide, and
(d) the isolated peptide of (a), (b) or (c), wherein the HLA antigen is HLA-A2.

In another embodiment, [4] and [5] of the present invention may be following [4'] and [5']:

[4'] An isolated peptide selected from the group consisting of:
(a) an isolated peptide that binds to an HLA antigen and induces cytotoxic T lymphocytes (CTLs), and which comprises an immunologically active fragment of the peptide consisting of the amino acid sequence of SEQ ID NO: 49,
(b) the isolated peptide of (a), wherein said immunologically active fragment comprises an amino acid sequence selected from the group consisting of SEQ ID NOs: 5, 7, 27 and 34,
(c) an isolated peptide that (i) comprises an amino acid sequence in which 1, 2, or several amino acid(s) are substituted, deleted, inserted, and/or added in the amino acid sequence of the peptide of (a) or (b), (ii) binds to an HLA antigen, and (iii) retains the CTL inducibility of the original peptide, and
(d) the isolated peptide of (a), (b) or (c), wherein the HLA antigen is HLA-A2,

[5'] The isolated peptide of [4], wherein said immunologically active fragment consists of an amino acid sequence selected from the group consisting of SEQ ID NOs: 5, 7, 27 and 34, further wherein the isolated peptide has one or both of the following characteristics:
(a) the second amino acid from the N-terminus is selected from the group consisting of leucine and methionine; and
(b) the C-terminal amino acid is selected from the group consisting of valine and leucine.

Objects and features of the invention will become more fully apparent when the following detailed description is read in conjunction with the accompanying figures and examples 1t is to be understood that both the foregoing summary of the present invention and the following detailed description are of exemplified embodiments, and not restrictive of the present invention or other alternate embodiments of the present invention.

In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments that follow.

A02-10-69 (SEQ ID NO: 27) and (c) SEMA5B-A02-10-370 (SEQ ID NO: 34). The quantity of IFN-gamma which CTL produced was measured by IFN-gamma enzyme-linked immunosorbent assay (ELISA). The results demonstrate that CTL line established by stimulation with each peptide show potent IFN-gamma production as compared with the control. In the figures, "+" indicates the IFN-gamma production against target cells pulsed with the appropriate peptide, and "−" indicates the IFN-gamma production against target cells not pulsed with any peptides. R/S ratio indicates the ratio of the number of responder cells (CTL line) and stimulator cells.

Figure 3:
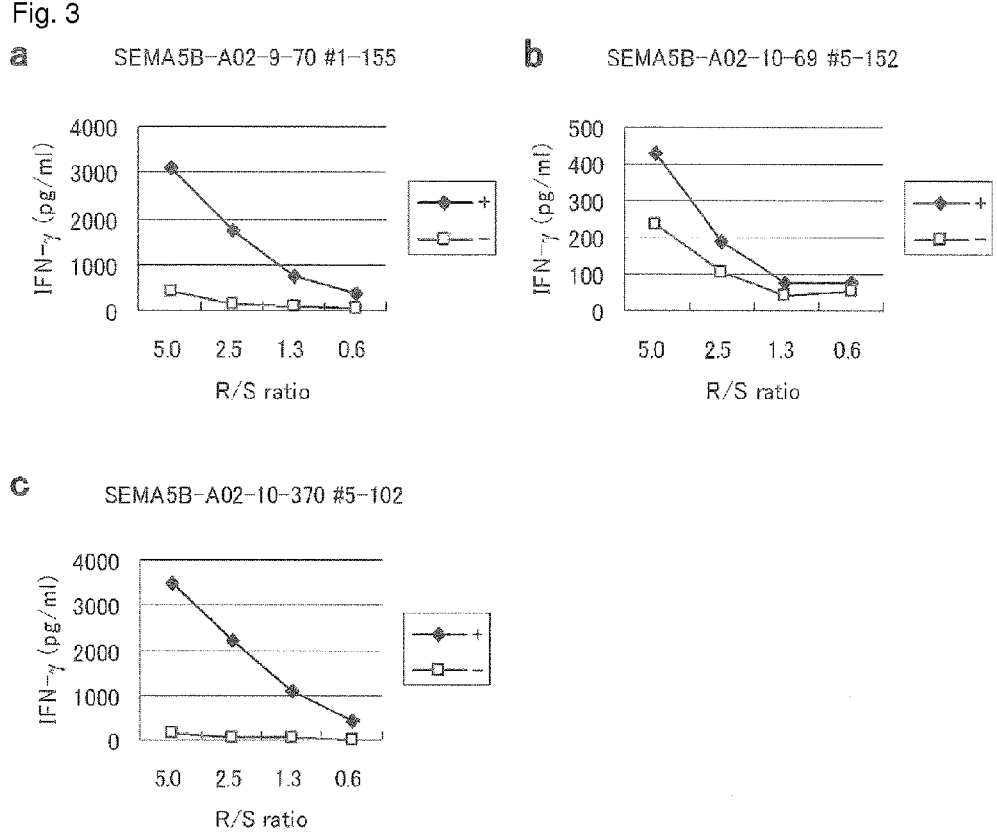

FIG. 3 is composed of a series of line graphs, (a) to (c), depicting the IFN-gamma production of the CTL clones established by limiting dilution from the CTL lines stimulated with (a) SEMA5B-A02-9-70 (SEQ ID NO: 5), (b) SEMA5B-A02-10-69 (SEQ ID NO: 27) and (c) SEMA5B-A02-10-370 (SEQ ID NO: 34). The results demonstrate that the CTL clones established by stimulation with each peptide show potent IFN-gamma production as compared with the control. In the figure, "+" indicates the IFN-gamma production against target cells pulsed with the appropriate peptide and "−" indicates the IFN-gamma production against target cells not pulsed with any peptides. R/S ratio indicates the ratio of the number of responder cells (CTL clone) and stimulator cells.

Figure 4:
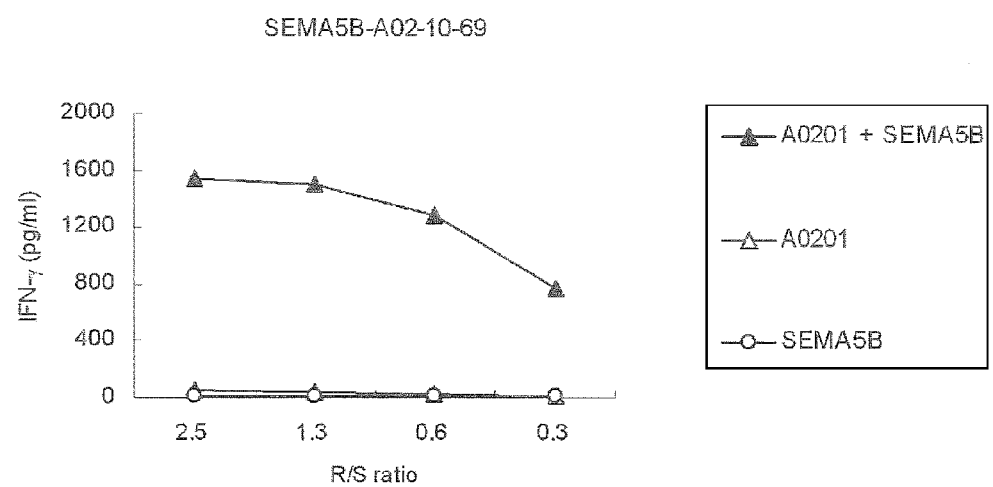

FIG. 4 is a line graph depicting specific CTL activity against target cells that exogenously express SEMA5B and HLA-A*0201. COS7 cells transfected with HLA-A*0201 or the full length of SEMA5B gene were prepared as controls. The CTL line established with SEMA5B-A02-10-69 (SEQ ID NO: 27) showed specific CTL activity against COS7 cells transfected with both SEMA5B and HLA-A*0201 (black triangle). On the other hand, no significant specific CTL activity was detected against target cells expressing either HLA-A*0201 (white triangle) or SEMA5B (white circle).

DESCRIPTION OF EMBODIMENTS

Although any methods and materials similar or equivalent to those described herein can be used in the practice or testing of embodiments of the present invention, the preferred methods, devices, and materials are now described. However, before the present materials and methods are described, it should be understood that these descriptions are merely illustrative only and not intended to be limiting. It should also be understood that the present invention is not limited to the particular sizes, shapes, dimensions, materials, methodologies, protocols, etc. described herein, as these may vary in accordance with routine experimentation and/or optimization. Furthermore, the terminology used in the description is for the purpose of describing the particular versions or embodiments only, and is not intended to limit the scope of the present invention that will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue or prior invention.

Unless otherwise defined, all technical and scientific terms used herein have the same meaning as commonly understood by one of ordinary skill in the art to which the present invention belongs. In case of conflict, the present specification, including definitions, will control. In addition, the materials, methods, and examples are illustrative only and not intended to be limiting.

I. Definitions

The words "a", "an", and "the" as used herein mean "at least one" unless otherwise specifically indicated.

The terms "isolated" and "purified" used in relation with a substance (e.g., peptide, antibody, polynucleotide, etc.) indicates that the substance is substantially free from at least one substance that may else be included in the natural source. Thus, an isolated or purified peptide refers to a peptide that are substantially free of cellular material such as carbohydrate, lipid, or other contaminating proteins from the cell or tissue source from which the peptide is derived, or substantially free of chemical precursors or other chemicals when chemically synthesized. The term "substantially free of cellular material" includes preparations of a peptide in which the peptide is separated from cellular components of the cells from which it is isolated or recombinantly produced. Thus, a peptide that is substantially free of cellular material includes preparations of polypeptide having less than about 30%, 20%, 10%, or 5% (by dry weight) of heterologous protein (also referred to herein as a "contaminating protein"). When the peptide is recombinantly produced, it is also preferably substantially free of culture medium, which includes preparations of peptide with culture medium less than about 20%, 10%, or 5% of the volume of the peptide preparation. When the peptide is produced by chemical synthesis, it is preferably substantially free of chemical precursors or other chemicals, which includes preparations of peptide with chemical precursors or other chemicals involved in the synthesis of the peptide less than about 30%, 20%, 10%, 5% (by dry weight) of the volume of the peptide preparation. That a particular peptide preparation contains an isolated or purified peptide can be shown, for example, by the appearance of a single band following sodium dodecyl sulfate (SDS)-polyacrylamide gel electrophoresis of the protein preparation and Coomassie Brilliant Blue staining or the like of the gel. In a preferred embodiment, peptides and polynucleotides of the present invention are isolated or purified.

The terms "polypeptide", "peptide" and "protein" are used interchangeably herein to refer to a polymer of amino acid residues. The terms apply to amino acid polymers in which one or more amino acid residue(s) may be modified residue(s), or non-naturally occurring residue(s), such as artificial chemical mimetic(s) of corresponding naturally occurring amino acid(s), as well as to naturally occurring amino acid polymers.

The term "oligopeptide" sometimes used in the present specification is used to refer to peptides of the present invention which are 20 residues or fewer, typically 15 residues or fewer in length and is typically composed of between about 8 and about 11 residues, often 9 or 10 residues. The latter are referred to herein as "nonapeptides" and "decapeptides", respectively.

The term "amino acid" as used herein refers to naturally occurring and synthetic amino acids, as well as amino acid analogs and amino acid mimetics that similarly function to the naturally occurring amino acids. Amino acid may be either L-amino acids or D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have one or more modified R group(s) or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotide" and "nucleic acid" are used interchangeably herein and, unless otherwise specifically indicated are similarly to the amino acids referred to by their commonly accepted single-letter codes.

The terms "agent" and "composition" are used interchangeably herein to refer to a product that includes the specified ingredients in the specified amounts, as well as any product that results, directly or indirectly, from combination of the specified ingredients in the specified amounts. Such terms, when used in relation to the modifier "pharmaceutical" (as in "pharmaceutical agent" and "pharmaceutical composition") are intended to encompass a product that includes the active ingredient(s), and any inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, in the context of the present invention, the terms "pharmaceutical agent" and "pharmaceutical composition" refer to any product made by admixing a molecule or compound of the present invention and a pharmaceutically or physiologically acceptable carrier.

The phrase "pharmaceutically acceptable carrier" or "physiologically acceptable carrier", as used herein, means a pharmaceutically or physiologically acceptable material, composition, substance or vehicle, including but not limited to, a liquid or solid filler, diluent, excipient, solvent or encapsulating material.

The pharmaceutical agents or compositions of the present invention find particular use as vaccines. In the context of the present invention, the phrase "vaccine" (also referred to as an "immunogenic composition") refers to an agent or a composition that has the function to induce anti-tumor immunity upon inoculation into animals.

The term "active ingredient" herein refers to a substance in an agent or composition that is biologically or physiologically active. Particularly, in the context of pharmaceutical agent or composition, the term "active ingredient" refers to a substance that shows an objective pharmacological effect. For example, in case of pharmaceutical agents or compositions for use in the treatment or prevention of cancer, active ingredients in the agents or compositions may lead to at least one biological or physiological action on cancer cells and/or tissues directly or indirectly. Preferably, such action may include reducing or inhibiting cancer cell growth, damaging or killing cancer cells and/or tissues, and so on. Typically, indirect effect of active ingredients is inductions of CTLs recognizing or killing cancer cells. Before being formulated, the "active ingredient" may also be referred to as "bulk", "drug substance" or "technical product".

Unless otherwise defined, the term "cancer" refers to the cancers over-expressing SEMA5B gene, examples of which include, but are not limited to, esophageal cancer, NSCLC, RCC and SCLC.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor/cancer cells, virus-infected cells) and inducing the death of such cells.

Unless otherwise defined, the term "HLA-A2", as used herein, representatively refers to the subtypes, examples of which include, but are not limited to, HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

As used herein, in the context of a subject or patient, the phrase "subject's (or patient's) HLA antigen is HLA-A2" refers to that the subject or patient homozygously or heterozygously possess HLA-A2 antigen gene as the MHC (major histocompatibility complex) Class I molecule, and HLA-A2 antigen is expressed in cells of the subject or patient as an HLA antigen.

To the extent that the methods and compositions of the present invention find utility in the context of the "treatment" of cancer, a treatment is deemed "efficacious" if it leads to clinical benefit such as decrease in size, prevalence, or metastatic potential of the cancer in the subject, survival time, suppression of postoperative recurrence and so on. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

In the context of the present invention, the treatment and/or prophylaxis of cancer and/or the prevention of postoperative recurrence thereof include any activity that leads to, for example, following events, such as the surgical removal of cancer cells, the inhibition of the growth of cancerous cells, the involution or regression of a tumor, the induction of remission and suppression of occurrence of cancer, the tumor regression, and the reduction or inhibition of metastasis, the suppression of post operative recurrence of cancer, and prolongation of survival time. Effective treatment and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multi-specific antibodies (e.g. bispecific antibodies) formed from at least two intact antibodies, and antibody fragments so long as they exhibit the desired biological activity. An "antibody" indicates all classes (e.g. IgA, IgD, IgE, IgG and IgM).

II. Peptides

Peptides of the present invention described in detail below may be referred to as "SEMA5B peptide(s)" or "SEMA5B polypeptide(s)".

To demonstrate that peptides derived from SEMA5B function as an antigen recognized by CTLs, peptides derived from SEMA5B (SEQ ID NO: 49) were analyzed to determine whether they were antigen epitopes restricted by HLA-A2 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994).

Candidates of HLA-A2 binding peptides derived from SEMA5B were identified based on their binding affinities to HLA-A2. The following candidate peptides were identified:

SEMA5B-A2-9-330 (SEQ ID NO: 1)
SEMA5B-A2-9-450 (SEQ ID NO: 2),
SEMA5B-A2-9-69 (SEQ ID NO: 3),
SEMA5B-A2-9-1045 (SEQ ID NO: 4),
SEMA5B-A2-9-70 (SEQ ID NO: 5),
SEMA5B-A2-9-287 (SEQ ID NO: 6),
SEMA5B-A2-9-1049 (SEQ ID NO: 7),
SEMA5B-A2-9-447 (SEQ ID NO: 9),
SEMA5B-A2-9-592 (SEQ ID NO: 10),
SEMA5B-A2-9-281 (SEQ ID NO: 11),
SEMA5B-A2-9-52 (SEQ ID NO: 12),
SEMA5B-A2-9-543 (SEQ ID NO: 13),
SEMA5B-A2-9-24 (SEQ ID NO: 14),
SEMA5B-A2-9-35 (SEQ ID NO: 15),
SEMA5B-A2-9-313 (SEQ ID NO: 16),
SEMA5B-A2-9-155 (SEQ ID NO: 17),
SEMA5B-A2-9-648 (SEQ ID NO: 18),
SEMA5B-A2-9-68 (SEQ ID NO: 19),
SEMA5B-A2-9-218 (SEQ ID NO: 20),
SEMA5B-A2-9-43 (SEQ ID NO: 21),
SEMA5B-A2-9-148 (SEQ ID NO: 22),
SEMA5B-A2-9-31 (SEQ ID NO: 23),
SEMA5B-A2-9-590 (SEQ ID NO: 24),
SEMA5B-A2-10-449 (SEQ ID NO: 25),
SEMA5B-A2-10-145 (SEQ ID NO: 26),
SEMA5B-A2-10-69 (SEQ ID NO: 27),
SEMA5B-A2-10-1045 (SEQ ID NO: 28),
SEMA5B-A2-10-58 (SEQ ID NO: 29),
SEMA5B-A2-10-533 (SEQ ID NO: 30),
SEMA5B-A2-10-42 (SEQ ID NO: 31),
SEMA5B-A2-10-68 (SEQ ID NO: 32),
SEMA5B-A2-10-508 (SEQ ID NO: 33),
SEMA5B-A2-10-370 (SEQ ID NO: 34),
SEMA5B-A2-10-539 (SEQ ID NO: 35),
SEMA5B-A2-10-38 (SEQ ID NO: 36),
SEMA5B-A2-10-441 (SEQ ID NO: 37),
SEMA5B-A2-10-35 (SEQ ID NO: 38),
SEMA5B-A2-10-484 (SEQ ID NO: 39),
SEMA5B-A2-10-137 (SEQ ID NO: 40),
SEMA5B-A2-10-148 (SEQ ID NO: 41),
SEMA5B-A2-10-479 (SEQ ID NO: 42),
SEMA5B-A2-10-243 (SEQ ID NO: 43),
SEMA5B-A2-10-106 (SEQ ID NO: 44),
SEMA5B-A2-10-60 (SEQ ID NO: 45),
SEMA5B-A2-10-281 (SEQ ID NO: 46) and
SEMA5B-A2-10-592 (SEQ ID NO: 47).

Moreover, after in vitro stimulation of T-cells by dendritic cells (DCs) pulsed (loaded) with these peptides, CTLs were successfully established by stimulating the DCs with each of the following peptides;

SEMA5B-A2-9-70 (SEQ ID NO: 5),
SEMA5B-A2-9-1049 (SEQ ID NO: 7),
SEMA5B-A2-10-69 (SEQ ID NO: 27) and
SEMA5B-A2-10-370 (SEQ ID NO: 34).

These established CTLs showed potent specific CTL activity against target cells pulsed with respective peptides. These results demonstrate that SEMA5B is an antigen recognized by CTLs and that the peptides tested are epitope peptides of SEMA5B restricted by HLA-A2.

Thus, the present invention provides nonapeptides (peptides composed of nine amino acid residues) and decapeptides (peptides composed of ten amino acid residues) of CTL-recognized epitopes from SEMA5B. Alternatively, the present invention provides isolated peptides which bind to HLA antigens and induce cytotoxic T lymphocytes (CTLs), wherein the peptide is composed of an immunologically active fragment of SEMA5B (SEQ ID NO: 49). More specifically, in some embodiments, the present invention provides peptides including an amino acid sequence selected from among SEQ ID NOs: 5, 7, 27 and 34. In preferred embodiments, the peptides of the present invention are peptides composed of an amino acid sequence selected from among SEQ ID NOs: 5, 7, 27 and 34.

Generally, software programs now available, for example, on the Internet, such as those described in Parker K C et al., J Immunol 1994 Jan. 1, 152(1): 163-75 and Nielsen M et al., Protein Sci 2003; 12: 1007-17 can be used to calculate the binding affinities between various peptides and HLA antigens in silico. Binding affinity with HLA antigens can be measured as described, for example, in Parker K C et al., J Immunol 1994 Jan. 1, 152(1): 163-75, Kuzushima K et al., Blood 2001, 98(6): 1872-81, Larsen M V et al. BMC Bioinformatics. 2007 Oct. 31; 8: 424, Buus S et al. Tissue Antigens., 62:378-84, 2003, Nielsen M et al., Protein Sci 2003; 12: 1007-17, and Nielsen M et al. PLoS ONE 2007; 2: e796, which are summarized in, e.g., Lafuente E M et al., Current Pharmaceutical Design, 2009, 15, 3209-3220. Methods for determining binding affinity are described, for example, in the Journal of Immunological Methods (1995, 185: 181-190) and Protein Science (2000, 9: 1838-1846). Therefore, one of skill in the art can use such software programs to select those fragments derived from SEMA5B, that have high binding affinity with HLA antigens. Accordingly, the present invention encompasses peptides composed of any fragments derived from SEMA5B, which would be determined to bind with HLA antigens by such known programs. Furthermore, such peptides may include the peptide composed of the full length of SEMA5B.

The peptides of the present invention, particularly the nonapeptides and decapeptides of the present invention, may be flanked with additional amino acid residues so long as the peptides retain their CTL inducibility. The particular additional amino acid residues may be composed of any kind of amino acids so long as they do not impair the CTL inducibility of the original peptide. Thus, the present invention encompasses peptides having CTL inducibility and a binding affinity for HLA antigens, in particular peptides derived from SEMA5B. Such peptides are, for example, less than about 40 amino acids, often less than about 20 amino acids, usually less than about 15 amino acids.

Generally, it is known that modifications of one, two, several or more amino acids in a peptide do not influence the function of the peptide, or in some cases even enhance the desired function of the original peptide. In fact, modified peptides (i.e., peptides composed of an amino acid sequence modified by substituting, inserting, deleting and/or adding one, two or several amino acid residues to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment of the present invention, the peptide having CTL inducibility of the present invention may be composed of a peptide having an amino acid sequence selected from among SEQ ID NOs: 5, 7, 27 and 34, in which one, two or several amino acids are added, deleted, inserted and/or substituted. In another embodiment, the peptides of the present invention may be peptides comprising an amino acid sequence in which one, two, or several amino acid(s) are substituted, deleted, inserted, and/or added in the amino acid sequence selected from among SEQ ID NOs: 5, 7, 27 and 34, provided the modified peptide retains the CTL inducibility of the original peptide.

Those of skill in the art will recognize that individual modifications (i.e., additions, insertions, deletions and/or substitutions) to an amino acid sequence that alter a single amino acid or a small percentage of the overall amino acid sequence tend to result in the conservation of the properties of the original amino acid side-chain. As such, they are conventionally referred to as "conservative substitution" or "conservative modification", wherein the alteration of a protein results in a protein with similar functions. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic group containing side-chain (H, F, Y, W). In addition, the following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, the peptide of the present invention is not restricted thereto and may include non-conservative modifications, so long as the resulting modified peptide retains the requisite CTL inducibility of the original unmodified peptide. Furthermore, the modified peptides should not exclude CTL inducible peptides derived from polymorphic variants, interspecies homologues, and alleles of SEMA5B.

Amino acid residues may be inserted, substituted, deleted and/or added to the peptides of the present invention or, alternatively, amino acid residues may be deleted therefrom to achieve a higher binding affinity. To retain the requisite CTL inducibility, one preferably modifies (inserts, deletes, add/or substitutes) only a small number (for example, 1, 2 or several) or a small percentage of amino acids. Herein, the term "several" means 5 or fewer amino acids, for example, 4 or 3 or fewer. The percentage of amino acids to be modified may be, for example, 20% or less, preferably 15% or less, more preferably 10% or less, even more preferably 1 to 5%.

When used in the context of cancer immunotherapy, the peptides of the present invention may be presented on the surface of a cell or exosome as a complex with an HLA antigen. Therefore, it is preferable to select peptides that not only induce CTLs but also possess high binding affinity to the HLA antigen. To that end, the peptides can be modified by substitution, insertion, deletion and/or addition of the amino acid residues to yield a modified peptide having improved binding affinity. In addition to peptides that are naturally displayed, since the regularity of the sequences of peptides displayed by binding to HLA antigens has already been known (J Immunol 1994, 152: 3913; Immunogenetics 1995, 41: 178; J Immunol 1994, 155: 4307), modifications based on such regularity may be introduced into the immunogenic peptides of the present invention.

For example, peptides exhibiting high HLA-A2 binding affinity tend to have the second amino acid from the N-terminus substituted with leucine or methionine. Likewise, peptides in which the C-terminal amino acid is substituted with valine or leucine can also be favorably used. Thus, peptides having an amino acid sequence selected from among SEQ ID NOs: 5, 7, 27 and 34 in which the second amino acid from the N-terminus of the amino acid sequence of the SEQ ID NO is substituted with leucine or methionine, and/or in which the C-terminus of the amino acid sequence of the SEQ ID NO is substituted with valine or leucine are contemplated by the present invention. In another embodiment, the present invention encompasses peptides having an amino acid sequence in which the second amino acid from the N-terminus of the amino acid sequence selected from among of the SEQ ID NOs: 5, 7, 27 and 34 is substituted with leucine or methionine, and/or the C-terminus of the amino acid sequence of the SEQ ID NO is substituted with valine or leucine. In preferred embodiments, the peptides of the present invention is composed of an amino acid sequence in which the second amino acid from the N-terminus of the amino acid sequence selected from among the SEQ ID NOs: 5, 7, 27 and 34 is substituted with leucine or methionine, and/or the C-terminus of the amino acid sequence of the SEQ ID NO is substituted with valine or leucine.

In one embodiment, the present invention provides the peptides having CTL inducibility, wherein the peptides have general formula selected from the group consisting of (55) to (58) as follows:

(55)-corresponding to SEQ ID NO: 5-Leu [X1] Pro Ser Leu Thr Leu Leu [X2], (56)-corresponding to SEQ ID NO: 7-Gly [X1] Leu Thr Leu Ala Val Tyr [X2], (57)-corresponding to SEQ ID NO: 27-Leu [X1] Leu Pro Ser Leu Thr Leu Leu [X2], and (58)-corresponding to SEQ ID NO: 34-Leu [X1] Tyr Gly Val Phe Thr Thr Asn [X2].

In the general formula (55)-(58), [X1] is leucine or methionine, and [X2] is valine or leucine.

Further, the present invention also provides isolated peptide represented by the general formula (55)-(58) defined above, to which one, two, or several amino acids are added at either or both of N-terminus and C-terminus thereof. Alternatively, the present invention further provides isolated peptides represented by the general formula (55)-(58) from which one, two or several amino acid residues are deleted at either or both of N-terminus and C-terminus thereof.

Substitutions may be introduced not only at the terminal amino acids but also at the positions of potential T cell receptor (TCR) recognition sites of peptides. Several studies have demonstrated that a peptide with amino acid substitutions may have equal to or better function than that of the original, for example, CAP1, p53$_{(264-272)}$, Her-2/neu$_{(369-377)}$ or gp100$_{(209-217)}$ (Zaremba et al. Cancer Res. 57, 4570-4577, 1997, T. K. Hoffmann et al. J. Immunol. (2002) February 1; 168(3):1338-47, S. O. Dionne et al. Cancer Immunol immunother. (2003) 52: 199-206 and S. O. Dionne et al. Cancer Immunology, Immunotherapy (2004) 53, 307-314).

The present invention also contemplates the addition of one, two or several amino acids may also be added to the N and/or C-terminus of the peptides of the present invention. Such modified peptides exhibiting high HLA antigen binding affinity and retaining CTL inducibility are also included in the present invention.

For example, the present invention provides an isolated peptide of less than 14, 13, 12, 11, or 10 amino acids in length that binds an HLA antigen, has CTL inducibility, and comprises the amino acid sequence selected from the group consisting of:

(i) an amino acid sequence selected from the group consisting of SEQ ID NOs: 5 and 7 in which one, two or several amino acid(s) are modified, and (ii) the amino acid sequence of (i), wherein the amino acid sequence has one or both of the following characteristics:

(a) the second amino acid from the N-terminus of said SEQ ID NO is or is modified to be leucine or methionine; and (b) the C-terminal amino acid of said SEQ ID NO is or is modified to be valine or leucine.

The present invention also provides an isolated peptide of less than 15, 14, 13, 12, or 11 amino acids in length that binds an HLA antigen, has CTL inducibility, and comprises an amino acid sequence selected from the group consisting of:

(i') an amino acid sequence selected from the group consisting of SEQ ID NOs: 27 and 34 in which one, two or several amino acid(s) are modified, and (ii') the amino acid sequence of (i'), wherein the amino acid sequence has one or both of the following characteristics:

(a) the second amino acid from the N-terminus of said SEQ ID NO is or is modified to be leucine or methionine; and (b) the C-terminal amino acid of said SEQ ID NO is or is modified to be valine or leucine.

These peptides may be processed in an APC to present a peptide of (i), (ii), (i'), and (ii') thereon, when these peptides are contacted with, or introduced in an APC.

However, when the peptide sequence is identical to a portion of the amino acid sequence of an endogenous or exogenous protein having a different function, side effects such as autoimmune disorders or allergic symptoms against specific substances may be induced. Therefore, one can perform homology searches using available databases to avoid situations in which the sequence of the peptide matches the amino acid sequence of another protein. When it becomes clear from the homology searches that there exists not even a peptide with 1 or 2 amino acids difference to the objective peptide, the objective peptide may be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of a peptide to induce a CTL when presented on an antigen-presenting cell (APC). Further, "CTL inducibility" includes the ability of a peptide to induce CTL activation, CTL proliferation, promote lysis of target cells by CTL, and to increase IFN-gamma production by CTL.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation of APCs with the test peptides, mixing the APCs with CD8 positive T cells to induce CTLs, and then measuring the IFN-gamma against the target cells produced and released by CTLs. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependent on MHC(HLA) class II restricted T(H) response) can be used. Alternatively, the target cells may be radiolabeled with $^{51}$Cr and such, and cytotoxic activity of CTLs may be calculated from radioactivity released from the target cells. Alternatively, it may be examined by measuring IFN-gamma produced and released by CTLs in the presence of cells that carry immobilized peptides, and visualizing the inhibition zone on the media using anti-IFN-gamma monoclonal antibodies.

As a result of examining the CTL inducibility of the peptides as described above, it was discovered that nonapeptides and decapeptides selected from among those peptides having the amino acid sequence indicated by SEQ ID NOs: 5, 7, 27 and 34 showed particularly high CTL inducibility as well as high binding affinity to an HLA antigen. Thus, these peptides are exemplified as preferred embodiments of the present invention.

Furthermore, homology analysis results demonstrated that such peptides do not share significant homology with peptides derived from any other known human gene products. This lowers the possibility of unknown or undesired immune responses when used for immunotherapy. Therefore, also from this aspect, these peptides are useful for eliciting immunity against SEMA5B in cancer patients. Thus, the peptides of the present invention, preferably, peptides having an amino acid sequence selected from among SEQ ID NOs: 5, 7, 27 and 34 are encompassed by the present invention.

In addition to modification of the peptides of the present invention, as discussed above, the peptides of the present invention may be linked to other peptides, so long as the resulting linked peptide retains the requisite CTL inducibility of the original peptide and, more preferably, also retain the requisite HLA binding thereof. Examples of suitable "other" peptides include: the peptides of the present invention or the CTL inducible peptides derived from other TAAs. The peptide of the present invention can be linked to an "other" peptide directly or indirectly via a linker. The linkers between the peptides are well known in the art, for example, AAY (P. M. Daftarian et al., J Trans Med 2007, 5:26), AAA, NKRK (R. P. M. Sutmuller et al., J. Immunol. 2000, 165: 7308-7315) or K (S. Ota et al., Can Res. 62, 1471-1476, K. S. Kawamura et al., J. Immunol. 2002, 168: 5709-5715).

For example, peptides derived from non-SEMA5B tumor-associated antigens also can be used to increase immune response via HLA class I and/or class II. It is wellknown in the art that cancer cells can express more than one tumor associated gene. Accordingly, it is within the scope of routine experimentation for one of ordinary skill in the art to determine whether a particular subject expresses additional tumor-associated genes, and then to include HLA class I and/or HLA class II binding peptides derived from the expression products of such genes in SEMA5B compositions or vaccines of the present invention.

Examples of HLA class I and HLA class II binding peptides are known to those of ordinary skill in the art (for example, see Coulie, Stem Cells 13:393-403, 1995), and can be used in connection with the present invention in a like manner as those disclosed herein. One of ordinary skill in the art can prepare polypeptides including one or more SEMA5B peptides and one or more of the non-SEMA5B peptides, or nucleic acids encoding such polypeptides, using conventional molecular biology procedures.

The above described linked peptides are referred to herein as "polytopes", i.e., groups of two or more potentially immunogenic or immune response stimulating peptides that can be joined together in various arrangements (e.g., concatenated, overlapping). The polytope (or nucleic acid encoding the polytope) can be administered in accordance with standard immunization protocols, e.g., to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., Proc. Natl. Acad. Sci. USA 92(13):5845-5849, 1995; Gilbert et al., Nature Biotechnol. 15(12):1280-1284, 1997; Thomson et al., J. Immunol. 157(2):822-826, 1996; Tam et al., J. Exp. Med. 171(1):299-306, 1990). Polytopes containing various numbers and combinations of epitopes can be prepared and tested for recognition by CTLs and for efficacy in increasing an immune response.

The peptides of the present invention may be further linked to other substances, so long as they retain the requisite CTL inducibility. Illustrative examples of such "other" substances include, but are not limited to, peptides, lipids, sugar and sugar chains, acetyl groups, natural and synthetic polymers, etc. The peptides may contain modifications such as glycosylation, side chain oxidation, or phosphorylation, so long as the modifications do not destroy the biological activity of the peptides as described herein. These kinds of modifications may be performed to confer additional functions (e.g., targeting function, and delivery function) or to stabilize the polypeptide.

For example, to increase the in vivo stability of a polypeptide, it is known in the art to introduce D-amino acids, amino acid mimetics or unnatural amino acids; this concept may also be adopted for the present polypeptides. The stability of a polypeptide may be assayed in a number of ways. For instance, peptidases and various biological media, such as human plasma and serum, can be used to test stability (see, e.g., Verhoef et al., Eur J Drug Metab Pharmacokin 1986, 11: 291-302).

When the peptides of the present invention include a cysteine residue, the peptides tend to form dimers via a disulfide bond between SH groups of the cysteine residues. Therefore, dimers of the peptides of the present invention are also included in the peptides of the present invention.

Moreover, as noted above, among the modified peptides that are substituted, deleted, inserted and/or added by one, two or several amino acid residues, those having same or higher activity as compared to original peptides can be screened for or selected. The present invention, therefore, also provides the method of screening for or selecting modified peptides having same or higher activity as compared to originals. For example, the method may include steps of:

a: modifying (i.e., substituting, deleting, inserting or adding) at least one amino acid residue of a peptide of the present invention, b: determining the activity of the peptide modified in step (a), and c: selecting the peptide having same or higher activity as compared to the original peptide.

Herein, the activity may include MHC binding activity and APC or CTL inducibility. Preferably, the activity of the peptide is CTL inducibility.

III. Preparation of SEMA5B Peptides

The peptides of the present invention may be prepared using well known techniques. For example, the peptides may be prepared synthetically, by recombinant DNA technology or chemical synthesis. The peptides of the present invention may be synthesized individually or as longer polypeptides including two or more peptides. The peptides may be isolated, i.e., purified or isolated substantially free from other naturally occurring host cell proteins and fragments thereof, or any other chemical substances.

The peptides of the present invention may contain modifications, such as glycosylation, side chain oxidation, or phosphorylation, provided such modifications do not destroy the biological activity of the original peptides. Other illustrative modifications include incorporation of D-amino acids or other amino acid mimetics that may be used, for example, to increase the serum half-life of the peptides.

A peptide of the present invention may be obtained through chemical synthesis based on the selected amino acid sequence. For example, conventional peptide synthesis methods that may be adopted for the synthesis include:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the peptides of the present invention may be obtained adopting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. Such vectors and host cells are also provided by the present invention. The host cell is then cultured to produce the peptide of interest. The peptide may also be produced in vitro adopting an in vitro translation system.

IV. Polynucleotides

The present invention provides polynucleotides that encode any of the aforementioned peptides of the present invention. The polynucleotides of the present invention may include polynucleotides derived from the natural occurring SEMA5B gene (for example, GenBank Accession No.

NM_001031702 (SEQ ID NO: 48)) or those having a conservatively modified nucleotide sequences thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon may be altered to any of the corresponding codons described without altering the encoded polypeptide. Such nucleic acid variations, referred to in the art as "silent variations," represent one species of conservatively modified variant. Every nucleic acid sequence described herein as encoding a peptide also describes every possible silent variation of the nucleic acid. One of skill in the art will readily recognize that each codon in a nucleic acid (except AUG, which is ordinarily the only codon for methionine, and TGG, which is ordinarily the only codon for tryptophan) may be modified to yield a functionally identical molecule. Accordingly, each disclosed peptide-encoding nucleotide sequence represents an implicit disclosure of the silent variations associated therewith.

The polynucleotide of the present invention may be composed of DNA, RNA, and derivatives thereof. As is well known in the art, a DNA molecule is suitably composed of bases such as the naturally occurring bases A, T, C, and G, and T is replaced by U in an RNA. One of skill in the art will recognize that non-naturally occurring bases be included in polynucleotides, as well.

The polynucleotide of the present invention may encode multiple peptides of the present invention with or without intervening amino acid sequences. For example, the intervening amino acid sequence may provide a cleavage site (e.g., enzyme recognition sequence) of the polynucleotide or the translated peptides. Furthermore, the polynucleotide of the present invention may include any additional sequences to the coding sequence encoding the peptide of the present invention. For example, the polynucleotide of the present invention may be a recombinant polynucleotide that includes regulatory sequences required for the expression of the peptide or may be an expression vector (plasmid) with marker genes and such. In general, such recombinant polynucleotides may be prepared by the manipulation of polynucleotides through conventional recombinant techniques using, for example, polymerases and endonucleases.

Both recombinant and chemical synthesis techniques may be used to produce the polynucleotides of the present invention. For example, the polynucleotide of the present invention may be produced by insertion of the polynucleotide having the coding sequence of the peptide of the present invention into an appropriate vector, which may be expressed when transfected into a competent cell. Alternatively, the polynucleotide of the present invention may be amplified using PCR techniques or replicated in suitable hosts (see, e.g., Sambrook et al., Molecular Cloning: A Laboratory Manual, Cold Spring Harbor Laboratory, New York, 1989). Alternatively, the polynucleotide of the present invention may be synthesized using the solid phase techniques, as described in Beaucage S L & Iyer R P, Tetrahedron 1992, 48: 2223-311; Matthes et al., EMBO J. 1984, 3: 801-5.

V. Exosomes

The present invention further provides intracellular vesicles called exosomes, which present complexes formed between the peptides of the present invention and HLA antigens on their surface. Exosomes may be prepared, for example by using the methods detailed in Japanese Patent Application Kohyo Publications No. Hei 11-510507 and WO99/03499, and may be prepared using APCs obtained from patients who are subject to treatment and/or prevention. The exosomes of the present invention may be inoculated as vaccines, similarly to the peptides of the present invention.

The type of HLA antigens included in the complexes must match that of the subject requiring treatment and/or prevention. For example, for Japanese, HLA-A2, particularly HLA-A*0201 and HLA-A*0206 are often appropriate. The use of HLA-A2 type that is highly expressed among the Japanese and Caucasian is favorable for obtaining effective results, and subtypes such as HLA-A*0201 and HLA-A*0206 find use. Typically, in the clinic, the type of HLA antigen of the patient requiring treatment is investigated in advance, which enables appropriate selection of peptides having high levels of binding affinity to this antigen, or having CTL inducibility by antigen presentation. Furthermore, in order to obtain peptides showing high binding affinity and CTL inducibility, substitution, deletion, or addition of 1, 2, or several amino acids may be performed based on the amino acid sequence of the naturally occurring SEMA5B partial peptide.

When using the HLA-A2 type of HLA antigen for the exosome of the present invention, the peptides having an amino acid sequence of any one of SEQ ID NOs: 5, 7, 27 and 34 have particular utility. In some embodiments, the exosomes of the present invention present complexes of the peptide of the present invention and an HLA-A2 antigen on their surface. Typical examples of the HLA-A2 antigen contained in such complexes include, but are not limited to, HLA-A*0201 and HLA-A*0206.

VI. Antigen-Presenting Cells (APCS)

The present invention also provides isolated APCs that present complexes formed with HLA antigens and the peptides of the present invention on their surface. The APCs may be derived from patients who are subject to treatment and/or prevention, and may be administered as vaccines by themselves or in combination with other drugs including the peptides, exosomes, or CTLs of the present invention.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DCs are representative APCs having the strongest CTL inducing activity among APCs, DCs are suitable for the APCs of the present invention.

For example, the APCs of the present invention may be obtained by inducing DCs from peripheral blood monocytes and then contacting (stimulating) them with the peptides of the present invention in vitro, ex vivo or in vivo. When the peptides of the present invention are administered to a subject, APCs that present the peptides of the present invention are induced in the body of the subject. Therefore, the APCs of the present invention may be obtained by collecting the APCs from the subject after administering the peptides of the present invention to the subject. Alternatively, the APCs of the present invention may be obtained by contacting APCs collected from a subject with the peptide of the present invention.

The APCs of the present invention may be administered to a subject for inducing immune response against cancer in the subject by themselves or in combination with other drugs including the peptides, exosomes or CTLs of the present invention. For example, the ex vivo administration may include steps of:

a: collecting APCs from a first subject,
  b: contacting the APCs of step a, with the peptide of the present invention, and
  c: administering the APCs of step b to a second subject.

The first subject and the second subject may be the same individual, or may be different individuals. The APCs obtained by step b may be administered as a vaccine for treating and/or preventing cancer, examples of which include, but are not limited to, esophageal cancer, NSCLC, RCC and SCLC.

The present invention also provides a method or process for manufacturing a pharmaceutical composition for inducing APCs, wherein the method includes the step of admixing or formulating the peptide of the invention with a pharmaceutically acceptable carrier.

According to an aspect of the present invention, the APCs of the present invention have CTL inducibility. In the context of the APCs, the phrase "having CTL inducibility" refers to showing higher CTL inducibility than those of APCs contacted with no peptides. Such APCs having CTL inducibility may be prepared by a method which includes the step of transferring a polynucleotide encoding the peptide of the present invention to APCs in vitro as well as the method mentioned above. The introduced gene may be in the form of DNA or RNA. Examples of methods for introduction include, without particular limitations, various methods conventionally performed in this field, such as lipofection, electroporation, or calcium phosphate method may be used. More specifically, it may be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present partial peptides.

In some embodiments, the APCs of the present invention are APCs that present complexes of an HLA-A2 antigen and the peptide of the present invention on their surface. Typical examples of the HLA-A2 antigen contained in such complexes include, but are not limited to, HLA-A*0201 and HLA-A*0206.

VII. Cytotoxic T Lymphocytes (CTLS)

A CTL induced against any of the peptides of the present invention strengthens the immune response targeting cancer cells in vivo and thus may be used as vaccines similar to the peptides. Thus, the present invention provides isolated CTLs that are specifically induced or activated by any of the peptides of the present invention.

Such CTLs may be obtained by (1) administering the peptide(s) of the present invention to a subject, (2) contacting (stimulating) subject-derived APCs and CD8 positive T cells, or peripheral blood mononuclear leukocytes in vitro with the peptide(s) of the present invention, (3) contacting CD8 positive T cells or peripheral blood mononuclear leukocytes in vitro with the APCs or exosomes presenting a complex of an HLA antigen and the peptide on their surface or (4) introducing a polynucleotide encoding both of T cell receptor (TCR) subunits or polynucleotides encoding each of TCR subunits, wherein the TCR can bind a complex of the peptide of the present invention and HLA-A2 antigen on a cell surface. Such APCs or exosomes to be used in preparation of CTLs may be prepared by the methods described above. Details of the method of (4) is described below in section "VIII. T Cell Receptor (TCR)".

The CTLs of the present invention may be derived from patients who are subject to treatment and/or prevention, and may be administered by themselves or in combination with other drugs including the peptides, APCs or exosomes of the present invention for the purpose of regulating effects. The obtained CTLs act specifically against target cells presenting the peptides of the present invention, for example, the same peptides used for induction. The target cells may be cells that endogenously express SEMA5B, such as cancer cells, or cells that are transfected with the SEMA5B gene; and cells that present a peptide of the present invention on the cell surface due to stimulation by the peptide may also serve as targets of activated CTL attack.

In some embodiments, the CTLs of the present invention are CTLs that recognize cells presenting complexes of HLA-A2 antigen and the peptide of the present invention. In the context of the CTL, the phrase "recognize a cell" refers to binding a complex of HLA-A2 antigen and the peptide of the present invention on the cell surface via its TCR and showing specific cytotoxic activity against the cell. Herein, "specific cytotoxic activity" refers to showing cytotoxic activity against the cell presenting a complex of HLA-A2 antigen and the peptide of the present invention but not other cells. Typical examples of the HLA-A2 antigen contained in such complex include, but are not limited to, HLA-A*0201 and HLA-A*0206.

VIII. T Cell Receptor (TCR)

The present invention also provides a composition including polynucleotide encoding both of TCR subunits or polynucleotides encoding each of TCR subunits, wherein the TCR can bind to a complex of HLA-A2 antigen and the peptide of the present invention on a cell surface, and methods of using the same. Such TCR subunits have the ability to form TCRs that confer specificity to T cells against tumor cells expressing SEMA5B. By using the known methods in the art, the polynucleotides encoding each of alpha- and beta-chains of the TCR of the CTL induced with the peptides of the present invention can be identified (WO2007/032255 and Morgan et al., J Immunol, 171, 3288 (2003)). For example, the PCR method is preferred to analyze the TCR. The PCR primers for the analysis can be, for example, 5'-R primers (5'-gtctaccag-gcattcgcttcat-3') as 5' side primers (SEQ ID NO: 50) and 3-TRa-C primers (5'-tcagctggaccacagccgcagcgt-3') specific to TCR alpha chain C region (SEQ ID NO: 51), 3-TRb-C1 primers (5'-tcagaaatcctttctcttgac-3') specific to TCR beta chain C1 region (SEQ ID NO: 52) or 3-TRbeta-C2 primers (5'-ctagcctctggaatcctttctctt-3') specific to TCR beta chain C2 region (SEQ ID NO: 53) as 3' side primers, but not limited thereto. The derivative TCRs may bind target cells presenting the peptide of the present invention with high avidity, and optionally mediate efficient killing of target cells presenting the peptide of the present invention in vivo and in vitro.

The polynucleotide encoding both of the TCR subunits or polynucleotides encoding each of the TCR subunits may be incorporated into suitable vectors, e.g., retroviral vectors. These vectors are well known in the art. The polynucleotide or the vectors including them usefully may be transferred into a T cell (e.g., CD8 positive T cell), for example, a T cell from a patient. Advantageously, the present invention provides an off-the-shelf composition allowing rapid modification of a patient's own T cells (or those of another mammal) to rapidly and easily produce modified T cells having excellent cancer cell killing properties.

The specific TCR against the peptide of the present invention is a receptor capable of specifically recognizing a complex of the peptide of the present invention and HLA antigen, giving a T cell specific activity against a target cell presenting a complex of the peptide of the present invention and HLA antigen when the TCR is presented on the surface of the T cell. A specific recognition of the above complex may be confirmed by any known methods, and preferred methods include, for example, HLA multimer staining analysis using HLA molecules and peptides of the present invention, and ELISPOT assay. By performing the ELISPOT assay, it can be confirmed that a T cell expressing the TCR on the cell surface recognizes a cell by the TCR, and that the signal is transmitted intracellularly. The confirmation that the above-mentioned complex can give a T cell cytotoxic activity when the complex exists on the T cell surface may also be carried out by a known method. A preferred method includes, for example, the determination of cytotoxic activity against an HLA positive target cell, such as chromium release assay.

Also, the present invention provides CTLs which are prepared by transduction with the nucleic acids encoding the TCR subunits that bind to the SEMA5B peptide of, e.g., SEQ ID NOs: 5, 7, 27 and 34 in the context of HLA-A2.

The transduced CTLs are capable of homing to cancer cells in vivo, and may be expanded by well known culturing methods in vitro (e.g., Kawakami et al., J. Immunol., 142, 3452-3461 (1989)). The CTLs of the present invention may be used to form an immunogenic composition useful in either or both of the treatment and the prevention of cancer in a patient in need of therapy or protection (WO2006/031221).

IX. Pharmaceutical Compositions

Since SEMA5B expression is specifically elevated in cancer, examples of which esophageal cancer, NSCLC, RCC and SCLC, compared with normal tissue, the peptides or polynucleotides of the present invention may be used for the treatment and/or prophylaxis of cancer, and/or prevention of postoperative recurrence thereof. Thus, the present invention provides a pharmaceutical agent or composition formulated for the treatment and/or prophylaxis of cancer and/or prevention of a postoperative recurrence of such cancer, such agent or composition including one or more of the peptides, or polynucleotides of the present invention as an active ingredient. Alternatively, the peptides of the present invention may be expressed on the surface of any of the foregoing exosomes or cells, such as APCs for the use as pharmaceutical agents or compositions. In addition, the aforementioned CTLs that can recognize a cell presenting a complex of the peptides of the present invention and HLA antigen may also be used as the active ingredient of the pharmaceutical agents or compositions of the present invention. Accordingly, the present invention provide agents or compositions including at least one active ingredient selected from among:
 (a) one or more peptides of the present invention;
 (b) one or more polynucleotides encoding such a peptide as disclosed herein in an expressible form;
 (c) one or more APCs or exosomes of the present invention; and
 (d) one or more CTLs of the present invention.

The pharmaceutical agents or compositions of the present invention find use as a vaccine. In the context of the present invention, the phrase "vaccine" (also referred to as an immunogenic composition) refers to a composition that has the function to improve, enhance and/or to induce anti-tumor immunity upon inoculation into animals. In other words, the present invention provides pharmaceutical agents or compositions for inducing an immune response against cancer in a subject.

The pharmaceutical agents or compositions of the present invention can be used to treat and/or prevent cancers, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal. In some embodiments, the pharmaceutical agents or compositions of the present invention can be formulated for the administration to a subject whose HLA antigen is HLA-A2.

In another embodiment, the present invention also provides the use of an active ingredient in the manufacture of a pharmaceutical agent or composition formulated for the treatment and/or prevention of cancer, and/or the prevention of a post-operative recurrence thereof, said active ingredient selected from among:
 (a) a peptide of the present invention;
 (b) a polynucleotide encoding such a peptide as disclosed herein in an expressible form;
 (c) an APC or an exosome presenting a peptide of the present invention on its surface; and
 (d) a cytotoxic T cell of the present invention.

Alternatively, the present invention further provides an active ingredient for use in treating and/or preventing cancer or tumor, and/or preventing a post-operative recurrence thereof said active ingredient selected from among:
 (a) a peptide of the present invention;
 (b) a polynucleotide encoding such a peptide as disclosed herein in an expressible form;
 (c) an APC or an exosome presenting a peptide of the present invention on its surface; and
 (d) a cytotoxic T cell of the present invention.

Alternatively, the present invention further provides a method or process for manufacturing a pharmaceutical composition or agent for treating and/or preventing cancer or tumor, and/or preventing a post-operative recurrence thereof, wherein the method or process includes the step of formulating a pharmaceutically or physiologically acceptable carrier with an active ingredient selected from among:
 (a) a peptide of the present invention;
 (b) a polynucleotide encoding such a peptide as disclosed herein in an expressible form;
 (c) an APC or an exosome presenting a peptide of the present invention on its surface; and
 (d) a cytotoxic T cell of the present invention.

In another embodiment, the present invention also provides a method or process for manufacturing a pharmaceutical composition or agent for treating and/or preventing cancer or tumor, and/or preventing a post-operative recurrence thereof, wherein the method or process includes the steps of admixing an active ingredient with a pharmaceutically or physiologically acceptable carrier, wherein the active ingredient is selected from among:
 (a) a peptide of the present invention;
 (b) a polynucleotide encoding such a peptide as disclosed herein in an expressible form;
 (c) an APC or an exosome presenting a peptide of the present invention on its surface; and
 (d) a cytotoxic T cell of the present invention.

In another embodiment, the present invention also provides a method for treating and/or preventing cancer or tumor, and/or preventing a post-operative recurrence thereof, wherein the method comprises the step of administering to a subject at least one active ingredient selected from among:
 (a) a peptide of the present invention;
 (b) a polynucleotide encoding such a peptide as disclosed herein in an expressible form;
 (c) an APC or an exosome presenting a peptide of the present invention on its surface; and
 (d) a cytotoxic T cell of the present invention.

According to the present invention, peptides having an amino acid sequence selected from among SEQ ID NOs: 5, 7, 27 and 34 have been found to be HLA-A2 restricted epitope peptides and the candidates that may induce potent and specific immune response against cancer expressing HLA-A2 and SEMA5B in a subject. Therefore, the pharmaceutical agents or compositions which include any of these peptides with the amino acid sequences of SEQ ID NOs: 5, 7, 27 and 34 are particularly suited for the administration to subjects whose HLA antigen is HLA-A2. The same applies to pharmaceutical agents or compositions which include polynucleotides encoding any of these peptides (i.e., the polynucleotides of the present invention).

Cancers to be treated by the pharmaceutical agents or compositions of the present invention are not limited and include any cancer in which SEMA5B is involved (e.g., is overexpressed), examples of which include, but not limited to, esophageal cancer, NSCLC, RCC and SCLC.

The pharmaceutical agents or compositions of the present invention may contain, in addition to the aforementioned active ingredients, other peptides that have the ability to induce CTLs against cancerous cells, other polynucleotides encoding the other peptides, other cells that present the other peptides, or such. Examples of such "other" peptides having the ability to induce CTLs against cancerous cells include, but are not limited to, cancer specific antigens (e.g., identified TAAs).

If necessary, the pharmaceutical agents or compositions of the present invention may optionally include other therapeutic substances as an active ingredient, so long as the substance does not inhibit the antitumoral effect of the active ingredient of the present invention, e.g., the peptide, polynucleotide, exosome, APC, CTL of the present invention. For example, formulations may include anti-inflammatory substances pain killers, chemotherapeutics, and the like. In addition to other therapeutic substances in the medicament itself, the medicaments of the present invention may also be administered sequentially or concurrently with the one or more other pharmacologic substances or compositions. The amounts of medicament and pharmacologic substance or composition depend, for example, on what type of pharmacologic substance(s) or composition(s) is/are used, the disease being treated, and the scheduling and routes of administration.

Those of skill in the art will readily recognize that, in addition to the ingredients particularly mentioned herein, the pharmaceutical agents or compositions of the present invention may include other agents, substances or compositions conventional in the art having regard to the type of formulation in question (e.g., fillers, binders, diluents, excipients, etc.).

In one embodiment of the present invention, the present pharmaceutical agents or compositions may be packaged in articles of manufacture, e.g., as kits containing materials useful for treating the pathological conditions of the disease to be treated, e.g., cancer. The article of manufacture may include a container of any of the present pharmaceutical agents or compositions with a label. Suitable containers include bottles, vials, and test tubes. The containers may be formed from a variety of materials, such as glass or plastic. The label on the container should indicate the agent or composition is used for treating or prevention of one or more conditions of the disease. The label may also indicate directions for administration and so on.

In addition to the container described above, a kit including a pharmaceutical agent or composition of the present invention may optionally further include a second container housing a pharmaceutically-acceptable diluent. It may further include other materials desirable from a commercial and user standpoint, including other buffers, diluents, filters, needles, syringes, and package inserts with instructions for use.

The pharmaceutical agents or compositions of the present invention can, if desired, be packaged in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical compositions containing the peptides as the active ingredient:

The peptides of the present invention can be administered directly as a pharmaceutical agent or composition, or if necessary, that may be formulated by conventional formulation methods. In the latter case, in addition to the peptides of the present invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical agents or compositions of the present invention can contain as necessary, stabilizers, suspensions, preservatives, surfactants and such. The pharmaceutical agents or compositions of the present invention can be used for anticancer purposes.

The peptides of the present invention can be prepared in combination, which includes two or more of peptides of the present invention, to induce CTL in vivo. The peptides can be in a cocktail or can be conjugated to each other using standard techniques. For example, the peptides can be chemically linked or expressed as a single fusion polypeptide sequence that may have one or several amino acid(s) as a linker (e.g., Lysine linker: K. S. Kawamura et al. J. Immunol. 2002, 168: 5709-5715). The peptides in the combination can be the same or different. By administering the peptides of the present invention, the peptides are presented in high density by the HLA antigens on APCs, then CTLs that specifically react toward the complex formed between the displayed peptide and the HLA antigen are induced. Alternatively, APCs (e.g., DCs) may be removed from a subject and then stimulated by the peptides of the present invention to obtain APCs that present any of the peptides of the present invention on their cell surface. These APCs can be re-administered to the subject to induce CTLs in the subject, and as a result, aggressiveness towards the tumor-associated endothelium can be increased.

The pharmaceutical agents or compositions for the treatment and/or prevention of cancer, that include any of the peptides of the present invention as the active ingredient, can also include an adjuvant so that cellular immunity will be established effectively. Alternatively, the pharmaceutical agent or composition of the present invention can be administered with other active ingredients or can be administered by formulation into granules. An adjuvant refers to any compound, substance or composition that enhances the immune response against the protein when administered together (or successively) with the protein having immunological activity. An adjuvant that can be applied includes those described in the literature (Clin Microbiol Rev 1994, 7: 277-89). Exemplary adjuvants include aluminum phosphate, aluminum hydroxide, alum, cholera toxin, salmonella toxin, Incomplete Freund's adjuvant (IFA), Complete Freund's adjuvant (CFA), ISCOMatrix, GM-CSF, CpG, O/W emulsion, and such, but are not limited thereto.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Preferable examples of the salts include salts with an alkali metal, salts with a metal, salts with an organic base, salts with an amine, salts with an organic acid (acetic acid, formic acid, propionic acid, fumaric acid, maleic acid, succinic acid, tartaric acid, citric acid, malic acid, oxalic acid, benzoic acid, methanesulfonic acid and so on) and salts with an inorganic acid (hydrochloric acid, phosphoric acid, hydrobromic acid, sulfuric acid and so on). As used herein, the phrase "pharmaceutically acceptable salt" refers to those salts that retain the biological effectiveness and properties of the compound and that are obtained by reaction with inorganic or organic acids or bases.

In some embodiments, the pharmaceutical agents or compositions of the present invention include a component which primes CTL. Lipids have been identified as substances capable of priming CTL in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinyl-seryl-serine (P3CSS) can be used to prime CTL when covalently attached to an appropriate peptide (see, e.g., Deres et al., Nature 1989, 342: 561-4).

Examples of suitable methods of administration include, but are not necessarily limited to, oral, intradermal, subcutaneous, intramuscular, intraosseous, peritoneal, and intravenous injection, or such, and systemic administration or local administration to the vicinity of the targeted sites. The administration can be performed by single administration or boosted by multiple administrations. The dose of the peptides of the present invention can be adjusted appropriately according to the disease to be treated, age of the patient, weight, method of administration, and such, and is ordinarily 0.001 mg to 1,000 mg, for example, 0.01 mg to 100 mg, for example, 0.1 mg to 10 mg, and can be administered once in a few days to few months. One skilled in the art can appropriately select a suitable dose.

(2) Pharmaceutical compositions containing polynucleotides as active ingredient:

The pharmaceutical agents or compositions of the present invention can also include nucleic acids encoding the peptide(s) disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors. See also, e.g., Wolff et al., Science 1990, 247: 1465-8; U.S. Pat. Nos. 5,580,859; 5,589,466; 5,804,566; 5,739,118; 5,736,524; 5,679,647; and WO 98/04720). Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a patient can be either direct, in which case the patient is directly exposed to a polynucleotide-carrying vector, or indirect, in which case, cells are first transformed with the polynucleotide of interest in vitro, then the cells are transplanted into the patient. These two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology that are applicable to the present invention are described by Ausubel et al., in Current Protocols in Molecular Biology, John Wiley & Sons, NY, 1993; and by Krieger, in Gene Transfer and Expression, A Laboratory Manual, Stockton Press, NY, 1990.

Like administration of peptides, administration of polynucleotides may be performed by oral, intradermal, subcutaneous, intravenous, intramuscular, intraosseous, and/or peritoneal injection, or such, e.g., systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of the present invention can be adjusted appropriately according to the disease to be treated, age of the patient, weight, method of administration, and such, and is or dinarily 0.001 mg to 1000 mg, for example, 0.01 mg to 100 mg, for example, 0.1 mg to 10 mg, and can be administered once every a few days to once every few months. One skilled in the art can appropriately select the suitable dose.

X. Methods Using the Peptides, Exosomes, APCS and CTLS

The peptides and polynucleotides of the present invention can be used for preparing or inducing APCs and CTLs. The exosomes and APCs of the present invention can be also used for inducing CTLs. The peptides, polynucleotides, exosomes and APCs can be used in combination with any other compounds so long as the additional compounds do not inhibit CTL inducibility. Thus, any of the aforementioned pharmaceutical agents or compositions of the present invention can be used for inducing CTLs. In addition thereto, those including the peptides and polynucleotides can be also used for inducing APCs as explained below.

(1) Methods of Inducing Antigen-Presenting Cells (APCs):

The present invention provides methods of inducing APCs with high CTL inducibility using the peptides or polynucleotides of the present invention.

The methods of the present invention include the step of contacting APCs with the peptides of the present invention in vitro, ex vivo or in vivo. For example, the method contacting APCs with the peptides of the present invention ex vivo can include steps of:

a: collecting APCs from a subject; and
b: contacting the APCs of step a with the peptide.

The APCs are not limited to a particular kind of cells and include DCs, Langerhans cells, macrophages, B cells, and activated T cells, which are known to present proteinaceous antigens on their cell surface so as to be recognized by lymphocytes. Preferably, DCs can be used since they have the strongest CTL inducibility among APCs. Any peptides of the present invention can be used by themselves or in combination with other peptides of the present invention or CTL inducible peptide derived from TAAs other than SEMA5B.

On the other hand, when the peptides of the present invention are administered to a subject, the APCs are contacted with the peptides in vivo, and consequently, the APCs with high CTL inducibility are induced in the body of the subject. Thus, the method of the present invention includes administering the peptides of the present invention to a subject to induce APCs with CTL inducibility in the body of the subject. Similarly, when the polynucleotides of the present invention are administered to a subject in an expressible form, the peptides of the present invention are expressed and contacted with APCs in vivo, and consequently, the APCs with high CTL inducibility are induced in the body of the subject. Thus, the method of the present invention may also include administering the polynucleotides of the present invention to a subject to induce APCs with CTL inducibility in the body of the subject. The phrase "expressible form" is described above in section "IX. Pharmaceutical Compositions, (2) Pharmaceutical compositions containing polynucleotides as the active ingredient".

Furthermore, the method of the present invention may include introducing the polynucleotide of the present invention into an APC to induce APC with CTL inducibility. For example, the method can include steps of:

a: collecting APCs from a subject; and
b: introducing a polynucleotide encoding the peptide of the present invention.

Step b can be performed as described above in section "VI. Antigen-Presenting Cells".

Alternatively, the present invention provides a method for preparing an antigen-presenting cell (APC) which specifically induces CTL activity against SEMA5B, wherein the method can include one of the following steps:

(a) contacting an APC with a peptide of the present invention in vitro, ex vivo or in vivo; and
(b) introducing a polynucleotide encoding a peptide of the present invention into an APC.

Alternatively, the present invention provides methods for inducing an APC having CTL inducibility, wherein the methods include the step selected from the group consisting of:

(a) contacting an APC with the peptide of the present invention, and
(b) introducing the polynucleotide encoding the peptide of the present invention into an APC.

The methods of the present invention can be carried out in vitro, ex vivo or in vivo. Preferably, the methods of the present invention can be carried out in vitro or ex vivo. APCs used for induction of APCs having CTL inducibility can be preferably APCs expressing HLA-A2 antigen. Such APCs can be prepared by the methods well-known in the arts from peripheral blood mononuclear cells (PBMCs) obtained from a subject whose HLA antigen is HLA-A2. The APCs induced by the method of the present invention can be APCs that present a complex of the peptide of the present invention and HLA antigen (HLA-A2 antigen) in their surface. When APCs induced by the method of the present invention are administered to a subject in order to induce immune responses against cancer in the subject, the subject is preferably the same one from whom APCs are derived. However, the subject may be a different one from the APC donor so long as the subject has the same HLA type with the APC donor.

In another embodiment, the present invention provide agents or compositions for use in inducing an APC having CTL inducibility, and such agents or compositions include one or more peptides or polynucleotides of the present invention.

In another embodiment, the present invention provides the use of the peptide of the present invention or the polynucleotide encoding the peptide in the manufacture of an agent or composition formulated for inducing APCs.

Alternatively, the present invention further provides the peptide of the present invention or the polypeptide encoding the peptide for use in inducing an APC having CTL inducibility.

(2) Methods of Inducing CTLs:

The present invention also provides methods for inducing CTLs using the peptides, polynucleotides, exosomes or APCs of the present invention.

The present invention also provides methods for inducing CTLs using a polynucleotide encoding both of TCR subunits or polynucleotides encoding each of TCR subunits, wherein the TCR can recognize (bind to) a complex of the peptide of the present invention and an HLA antigen presented on cell surface. Preferably, the methods for inducing CTLs may include at least one step selected from among:

a) contacting a CD8 positive T cell with an antigen-presenting cell and/or an exosome that presents on its surface a complex of an HLA antigen and a peptide of the preset invention; and b) introducing a polynucleotide encoding both of TCR subunits or polynucleotides encoding the each of TCR subunits into a CD8 positive T cell, wherein the TCR can recognize (bind to) a complex of a peptide of the present invention and an HLA antigen presented on a cell surface.

When the peptides, the polynucleotides, APCs, or exosomes of the present invention are administered to a subject, CTLs are induced in the body of the subject, and the strength of the immune response targeting cancer cells expressing SEMA5B is enhanced. Thus, the methods of the present invention can include the step of administering the peptides, the polynucleotides, the APCs or exosomes of the present invention to a subject.

Alternatively, CTLs can be also induced by using them ex vivo, and after inducing CTLs, the activated CTLs can be returned to the subject. For example, the method can include steps of:

a: collecting APCs from a subject;
b: contacting the APCs of step a, with the peptide of the present invention; and
c: co-culturing the APCs of step b with CD8 positive T cells.

The APCs to be co-cultured with the CD8 positive T cells in above step c can also be prepared by transferring a polynucleotide of the present invention into APCs as described above in section "VI. Antigen-Presenting Cells", though the present invention is not limited thereto, and thus encompasses any APCs that effectively present on their surface a complex of an HLA antigen and a peptide of the present invention.

One may optionally utilize exosomes that presents on its surface a complex of an HLA antigen and the peptide of the present invention instead of the afore-mentioned APCs. Namely, the present invention can include the step of co-culturing exosomes presenting on its surface a complex of an HLA antigen and the peptide of the present invention. Such exosomes can be prepared by the methods described above in section "V. Exosomes".

APCs or exosomes used for induction of CTLs can be preferably APCs or exosomes that present on their surface a complex of the peptide of the present invention and HLA-A2 antigen.

Furthermore, CTLs can be induced by introducing a polynucleotide encoding both of TCR subunits or polynucleotides encoding each of TCR subunits into a CD8 positive cell, wherein the TCR can bind to a complex of the peptide of the present invention and an HLA antigen presented on a cell surface. Such transduction can be performed as described above in section "VIII. T Cell Receptor (TCR)".

The methods of the present invention can be carried out in vitro, ex vivo or in vivo. Preferably, the methods of the present invention can be carried out in vitro or ex vivo. CD8 positive T cells used for induction of CTLs can be prepared by well-known methods in the art from PBMCs obtained from a subject. In preferred embodiments, a donor for CD8 positive T cells can be a subject whose HLA antigen is HLA-A2. The CTLs induced by the methods of the present invention can be CTLs that can recognize cells presenting a complex of the peptide of the present invention and an HLA antigen on its surface. When CTLs induced by the method of the present invention are administered to a subject in order to induce immune responses against cancer in the subject, the subject is preferably the same one from whom CD8 positive T cells are derived. However, the subject may be a different one from the CD8 positive T cell donor so long as the subject has the same HLA type with the CD8 positive T cell donor.

In addition, the present invention provides a method or process for manufacturing a pharmaceutical agent or composition for inducing CTLs, wherein the method or process includes the step of admixing or formulating the peptide of the present invention with a pharmaceutically acceptable carrier.

In another embodiment, the present invention provide an agent or composition for inducing CTL, wherein the agent or composition comprises one or more peptide(s), one or more polynucleotide(s), or one or more APCs or exosomes of the present invention.

In another embodiment, the present invention provides the use of the peptide, polynucleotide, or APC or exosome of the present invention in the manufacture of an agent or composition formulated for inducing a CTL.

Alternatively, the present invention further provides the peptide, polynucleotide, or APC or exosome of the present invention for use in inducing a CTL.

(3) Methods of Inducing Immune Response:

Moreover, the present invention provides methods of inducing an immune response against diseases related to SEMA5B. Suitable diseases may include cancer, examples of which include, but are not limited to, esophageal cancer, NSCLC, RCC and SCLC.

The methods of the present invention may include the step of administering agent(s) or composition(s) containing any of the peptides of the present invention or polynucleotides encoding them. The method of the present invention may also contemplate the administration of exosomes or APCs presenting any of the peptides of the present invention. For details, see the item of "IX. Pharmaceutical Compositions", particularly the part describing the use of the pharmaceutical agents and compositions of the present invention as vaccines. In addition, the exosomes and APCs that can be employed for the present methods for inducing immune response are described in detail under the items of "V. Exosomes", "VI. Antigen-Presenting Cells (APCs)", and (1) and (2) of "X. Methods using the Peptides, Exosomes, APCs and CTLs", supra.

In preferred embodiments, the subjects treated by the method of the present invention can be subjects whose HLA antigen is HLA-A2.

The present invention also provides a method or process for manufacturing a pharmaceutical agent or composition inducing immune response, wherein the method may include the step of admixing or formulating a peptide or polynucleotide of the present invention with a pharmaceutically acceptable carrier.

Alternatively, the method of the present invention may include the step of administrating a vaccine or a pharmaceutical composition of the present invention that contains:
(a) a peptide of the present invention;
(b) a nucleic acid (polynucleotide) encoding such a peptide as disclosed herein in an expressible form;
(c) an APC or an exosome presenting a peptide of the present invention on its surface; or
(d) a CTL of the present invention.

In the context of the present invention, a cancer over-expressing SEMA5B can be treated with these active ingredients. Examples of such cancer include, but are not limited to, esophageal cancer, NSCLC, RCC and SCLC. Accordingly, prior to the administration of the vaccines or pharmaceutical compositions including the active ingredients, it is preferable to confirm whether the expression level of SEMA5B in the cells or tissues to be treated is enhanced compared with normal cells of the same organ. Thus, in one embodiment, the present invention provides a method for treating cancer (over)expressing SEMA5B, which method may include the steps of:
i) determining the expression level of SEMA5B in cells or tissue(s) obtained from a subject with the cancer to be treated;
ii) comparing the expression level of SEMA5B with normal control; and
iii) administrating at least one component selected from among steps (a) to (d) described above to a subject with cancer over-expressing SEMA5B compared with normal control.

Alternatively, the present invention also provides a vaccine or pharmaceutical composition that includes at least one component selected from among (a) to (d) described above, for use in administrating to a subject having cancer over-expressing SEMA5B. In other words, the present invention further provides a method for identifying a subject to be treated with the SEMA5B polypeptide of the present invention, such method including the step of determining an expression level of SEMA5B in subject-derived cells or tissue(s), wherein an increase of the level compared to a normal control level of the gene indicates that the subject may have cancer which may be treated with the SEMA5B polypeptide of the present invention. The method of identifying a subject to be treated cancer of the present invention are described in more detail below.

Any subject-derived cell or tissue can be used for the determination of SEMA5B expression so long as it includes the objective transcription or translation product of SEMA5B. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from tissue suspected to be cancerous. Further, if necessary, the cell may be purified from the obtained bodily tissues and fluids, and then used as the subjected-derived sample.

A subject to be treated by the present method is preferably a mammal. Exemplary mammals include, but are not limited to, e.g., human, non-human primate, mouse, rat, dog, cat, horse, and cow.

According to the present invention, the expression level of SEMA5B in cells or tissues obtained from a subject may be determined. The expression level can be determined at the transcription (nucleic acid) product level, using methods known in the art. For example, the mRNA of SEMA5B may be quantified using probes by hybridization methods (e.g., Northern hybridization). The detection may be carried out on a chip, an array or as such. The use of an array may be preferable for detecting the expression level of SEMA5B. Those skilled in the art can prepare such probes utilizing the sequence information of SEMA5B. For example, the cDNA of SEMA5B may be used as the probes. If necessary, the probes may be labeled with a suitable label, such as dyes, fluorescent substances and isotopes, and the expression level of the gene may be detected as the intensity of the hybridized labels.

Furthermore, the transcription product of SEMA5B (e.g., SEQ ID NO: 49) may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of SEMA5B. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degrees C. lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degrees C. for short probes or primers (e.g., 10 to 50 nucleotides) and at least about 60 degrees C. for longer probes or primers. Stringent conditions may also be achieved with the addition of destabilizing substances, such as formamide.

A probe or primer of the present invention is typically a substantially purified oligonucleotide. The oligonucleotide typically includes a region of nucleotide sequence that hybridizes under stringent conditions to at least about 2000, 1000, 500, 400, 350, 300, 250, 200, 150, 100, 50, or 25, consecutive sense strand nucleotide sequence of a nucleic acid including a SEMA5B, or an anti-sense strand nucleotide sequence of a nucleic acid including a SEMA5B, or of a naturally occurring mutant of these sequences. In particular, for example, in a preferred embodiment, an oligonucleotide having 5-50 in length can be used as a primer for amplifying the genes, to be detected. More preferably, mRNA or cDNA of a SEMA5B gene can be detected with oligonucleotide probe or primer of a specific size, generally 15-30b in length. The size may range from at least 10 nucleotides, at least 12 nucleotides, at least 15 nucleotides, at least 20 nucleotides, at least 25 nucleotides, at least 30 nucleotides and the probes and primers may range in size from 5-10 nucleotides, 10-15 nucleotides, 15-20 nucleotides, 20-25 nucleotides and 25-30 nucleotides. In preferred embodiments, length of the oligonucleotide probe or primer can be selected from 15-25. Assay procedures, devices, or reagents for the detection of gene by using such oligonucleotide probe or primer are well known (e.g. oligonucleotide microarray or PCR). In these assays, probes or primers can also include tag or linker sequences. Further, probes or primers can be modified with detectable label or affinity ligand to be captured. Alternatively, in hybridization based detection procedures, a polynucleotide having a few hundreds (e.g., about 100-200) bases to a few kilo (e.g., about 1000-2000) bases in length can also be used for a probe (e.g., northern blotting assay or cDNA microarray analysis).

Alternatively, the translation product may be detected for the diagnosis of the present invention. For example, the quantity of SEMA5B protein (SEQ ID NO: 49) or the immunologically fragment thereof may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment or modified antibody retains the binding ability to the SEMA5B protein. Such antibodies against the peptides of the present invention and the fragments thereof are also provided by the present invention. Methods to prepare these kinds of antibodies for the detection of proteins are well known in the art, and any method may be employed in the present invention to prepare such antibodies and equivalents thereof.

As another method to detect the expression level of SEMA5B gene based on its translation product, the intensity of staining may be measured via immunohistochemical analysis using an antibody against the SEMA5B protein. Namely, in this measurement, strong staining indicates increased presence/level of the protein and, at the same time, high expression level of SEMA5B gene.

The expression level of a target gene, e.g., the SEMA5B gene, in cancer cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

The control level may be determined at the same time as the cancer cells using a sample(s) previously collected and stored from a subject(s) whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of SEMA5B gene in samples from subjects whose disease states are known. Furthermore, the control level can be derived from a database of expression patterns from previously tested cells. Moreover, according to an aspect of the present invention, the expression level of SEMA5B gene in a biological sample may be compared to multiple control levels, determined from multiple reference samples. It is preferred to use a control level determined from a reference sample derived from a tissue type similar to that of the subject-derived biological sample. Moreover, it is preferred to use the standard value of the expression levels of SEMA5B gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

When the expression level of SEMA5B gene is increased as compared to the normal control level, or is similar/equivalent to the cancerous control level, the subject may be diagnosed with cancer to be treated.

The present invention also provides a method of (i) diagnosing whether a subject suspected to have cancer to be treated, and/or (ii) selecting a subject for cancer treatment, which method may include the steps of:

a) determining the expression level of SEMA5B in cells or tissue(s) obtained from a subject who is suspected to have the cancer to be treated;

b) comparing the expression level of SEMA5B with a normal control level;

c) diagnosing the subject as having the cancer to be treated, if the expression level of SEMA5B is increased as compared to the normal control level; and d) selecting the subject for cancer treatment, if the subject is diagnosed as having the cancer to be treated, in step c).

Alternatively, such a method may include the steps of:

a) determining the expression level of SEMA5B in cells or tissue(s) obtained from a subject who is suspected to have the cancer to be treated;

b) comparing the expression level of SEMA5B with a cancerous control level;

c) diagnosing the subject as having the cancer to be treated, if the expression level of SEMA5B is similar or equivalent to the cancerous control level; and d) selecting the subject for cancer treatment, if the subject is diagnosed as having the cancer to be treated, in step c).

The present invention also provides a diagnostic kit for diagnosing or determining a subject who is or is suspected to be suffering from or at risk for a cancer that can be treated with the SEMA5B polypeptide of the present invention, which may also find use in assessing and/or monitoring the efficacy or applicability of a cancer immunotherapy. Preferably, the cancer includes, but is not limited to, esophageal cancer, NSCLC, RCC and SCLC. More particularly, the kit preferably may include at least one reagent for detecting the expression of the SEMA5B gene in a subject-derived cell, which reagent may be selected from the group of:

(a) a reagent for detecting an mRNA of the SEMA5B gene;

(b) a reagent for detecting the SEMA5B protein or the immunologically fragment thereof; and (c) a reagent for detecting the biological activity of the SEMA5B protein.

Examples of reagents suitable for the detection of mRNA of the SEMA5B gene may include nucleic acids that specifically bind to or identify the SEMA5B mRNA, such as oligonucleotides that have a complementary sequence to a portion of the SEMA5B mRNA. These kinds of oligonucleotides are exemplified by primers and probes that are specific to the SEMA5B mRNA. These kinds of oligonucleotides may be prepared based on methods well known in the art. If needed, the reagent for detecting the SEMA5B mRNA may be immobilized on a solid matrix. Moreover, more than one reagent for detecting the SEMA5B mRNA may be included in the kit.

On the other hand, examples of reagents suitable for the detection of the SEMA5B protein or the immunologically fragment thereof may include antibodies to the SEMA5B protein or the immunologically fragment thereof. The antibody may be monoclonal or polyclonal. Furthermore, any fragment or modification (e.g., chimeric antibody, scFv, Fab, $F(ab')_2$, Fv, etc.) of the antibody may be used as the reagent, so long as the fragment or modified antibody retains the binding ability to the SEMA5B protein or the immunologically fragment thereof. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the SEMA5B protein may be included in the kit.

The kit may contain more than one of the aforementioned reagents. The kit can further include a solid matrix and reagent for binding a probe against a SEMA5B gene or antibody against a SEMA5B peptide, a medium and container for culturing cells, positive and negative control reagents, and a secondary antibody for detecting an antibody against a SEMA5B peptide. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers may include bottles, vials, and test tubes. The containers may be formed from a variety of materials, such as glass or plastic.

In an embodiment of the present invention, when the reagent is a probe against the SEMA5B mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of SEMA5B mRNA present in the sample. The detection sites may be configured in any suitably detectable shape and are typically in the shape of a bar or dot spanning the width of a test strip.

The kit of the present invention may further include a positive control sample or SEMA5B standard sample. The positive control sample of the present invention may be prepared by collecting SEMA5B positive samples and then assaying their SEMA5B levels. Alternatively, a purified SEMA5B protein or polynucleotide may be added to cells that do not express SEMA5B to form the positive sample or the SEMA5B standard sample. In the context of the present invention, purified SEMA5B may be a recombinant protein. The SEMA5B level of the positive control sample is, for example, more than the cut off value.

In one embodiment, the present invention further provides a diagnostic kit including, a protein or a partial protein thereof specifically recognized by the antibody of the present invention or the fragment thereof.

Examples of partial peptides of the present invention include polypeptides composed of at least 8, preferably 15, and more preferably 20 contiguous amino acids in the amino acid sequence of a protein of the present invention. Cancer can be diagnosed by detecting an antibody in a sample (e.g., blood, tissue) using a protein or a peptide (polypeptide) of the present invention. The method for preparing the protein of the present invention and peptides are as described above.

The methods for diagnosing cancer of the present invention can be performed by determining the difference between the amount of anti-SEMA5B antibody and that in the corresponding control sample as describe above. The subject is suspected to be suffering from cancer, if cells or tissues of the subject contain antibodies against the expression products (SEMA5B) of the gene and the quantity of the anti-SEMA5B antibody is determined to be more than the cut off value in level compared to that in normal control.

In another embodiment, a diagnostic kit of the present invention may include the peptide of the present invention and an HLA molecule binding thereto. The method for detecting antigen specific CTLs using antigenic peptides and HLA molecules has already been established (for example, Altman J D et al., Science. 1996, 274(5284): 94-6). Thus, the complex of the peptide of the present invention and the HLA molecule can be applied to the detection method to detect tumor antigen specific CTLs, thereby enabling earlier detection, recurrence and/or metastasis of cancer. Further, it can be employed for the selection of subjects applicable with the pharmaceuticals including the peptide of the present invention as an active ingredient, or the assessment of the treatment effect of the pharmaceuticals.

Particularly, according to the known method (see, for example, Altman J D et al., Science. 1996, 274(5284): 94-6), the oligomer complex, such as tetramer, of the radiolabeled HLA molecule and the peptide of the present invention can be prepared. With using the complex, the diagnosis can be done, for example, by quantifying the antigen-peptide specific CTLs in the peripheral blood lymphocytes derived from the subject suspected to be suffering from cancer.

The present invention further provides methods and diagnostic agents for evaluating immunological response of subject by using peptide epitopes as described herein. In one embodiment of the invention, HLA-A2 restricted peptides as described herein may be used as reagents for evaluating or predicting an immune response of a subject. The immune response to be evaluated may be induced by contacting an immunogen with immunocompetent cells in vitro or in vivo. In certain embodiments, any substances or compositions that may result in the production of antigen specific CTLs that recognize and bind to the peptide epitope(s) may be employed as the reagent. The peptide reagents may need not to be used as the immunogen. Assay systems that are used for such an analysis include relatively recent technical developments such as tetramers, staining for intracellular lymphokines and interferon release assays, or ELISPOT assays. In preferred embodiments, the immunocompetent cells for evaluating an immunological response, may be selected from among peripheral blood, peripheral blood lymphocyte (PBL), and peripheral blood mononuclear cell (PBMC). Methods for collecting or isolating such immunocompetent cells are well known in the arts. In an alternate preferred embodiment, the immunocompetent cells to be contacted with peptide reagent include antigen presenting cells such as dendritic cells.

For example, peptides of the present invention may be used in tetramer staining assays to assess peripheral blood mononuclear cells for the presence of antigen-specific CTLs following exposure to a tumor cell antigen or an immunogen. The HLA tetrameric complex may be used to directly visualize antigen specific CTLs (see, e.g., Ogg et al., Science 279: 2103-2106, 1998; and Altman et al, Science 174: 94-96, 1996) and determine the frequency of the antigen-specific CTL population in a sample of peripheral blood mononuclear cells. A tetramer reagent using a peptide of the invention may be generated as described below.

A peptide that binds to an HLA molecule is refolded in the presence of the corresponding HLA heavy chain and beta 2-microglobulin to generate a trimolecular complex. In the complex, carboxyl terminal of the heavy chain is biotinylated at a site that was previously engineered into the protein. Then, streptavidin is added to the complex to form tetramer composed of the trimolecular complex and streptavidin. By means of fluorescently labeled streptavidin, the tetramer can be used to stain antigen specific cells. The cells can then be identified, for example, by flow cytometry. Such an analysis may be used for diagnostic or prognostic purposes. Cells identified by the procedure can also be used for therapeutic purposes.

The present invention also provides reagents to evaluate immune recall responses (see, e.g., Bertoni et al, J. Clin. Invest. 100: 503-513, 1997 and Penna et al., J. Exp. Med. 174: 1565-1570, 1991) including peptides of the present invention. For example, patient PBMC samples obtained from individuals with a cancer to be treated can be analyzed for the presence of antigen-specific CTLs using specific peptides. A blood sample containing mononuclear cells can be evaluated by cultivating the PBMCs and stimulating the cells with a peptide of the invention. After an appropriate cultivation period, the expanded cell population can be analyzed, for example, for CTL activity.

The peptides may also be used as reagents to evaluate the efficacy of a vaccine. PBMCs obtained from a patient vaccinated with an immunogen may be analyzed using, for example, either of the methods described above. The patient is HLA typed, and peptide epitope reagents that recognize the allele specific molecules present in the patient are selected for the analysis. The immunogenicity of the vaccine may be indicated by the presence of epitope-specific CTLs in the PBMC sample. The peptides of the invention may also be used to make antibodies, using techniques well known in the art (see, e.g., CURRENT PROTOCOLS IN IMMUNOL- OGY, Wiley/Greene, N.Y.; and Antibodies A Laboratory Manual, Harlow and Lane, Cold Spring Harbor Laboratory Press, 1989), which may find use as reagents to diagnose, detect or monitor cancer. Such antibodies may include those that recognize a peptide in the context of an HLA molecule, i.e., antibodies that bind to a peptide-MHC complex.

The peptides and compositions of the present invention have a number of additional uses, some of which are described herein. For instance, the present invention provides a method for diagnosing or detecting a disorder characterized by expression of a SEMA5B immunogenic polypeptide. These methods involve determining expression of a SEMA5B HLA binding peptide, or a complex of a SEMA5B HLA binding peptide and an HLA class I molecule in a biological sample. The expression of a peptide or complex of peptide and HLA class I molecule can be determined or detected by assaying with a binding partner for the peptide or complex. In an preferred embodiment, a binding partner for the peptide or complex may be an antibody recognizes and specifically bind to the peptide. The expression of SEMA5B in a biological sample, such as a tumor biopsy, can also be tested by standard PCR amplification protocols using SEMA5B primers. An example of tumor expression is presented herein and further disclosure of exemplary conditions and primers for SEMA5B amplification can be found in WO2003/27322, the contents of which are incorporated by reference herein.

Preferably, the diagnostic methods involve contacting a biological sample isolated from a subject with an agent specific for the SEMA5B HLA binding peptide to detect the presence of the SEMA5B HLA binding peptide in the biological sample. As used herein, "contacting" means placing the biological sample in sufficient proximity to the agent and under the appropriate conditions of, e.g., concentration, temperature, time, ionic strength, to allow the specific interaction between the agent and SEMA5B HLA binding peptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Optimal conditions for facilitating a specific interaction between a molecule and its cognate are described in U.S. Pat. No. 5,108,921, issued to Low et al., the contents of which are incorporated by reference herein.

The diagnostic method of the present invention can be performed in either or both of in vivo and in vitro. Accordingly, biological sample can be located in vivo or in vitro in the present invention. For example, the biological sample can be a tissue in vivo and the agent specific for the SEMA5B immunogenic polypeptide can be used to detect the presence of such molecules in the tissue. Alternatively, the biological sample can be collected or isolated in vitro (e.g., a blood sample, tumor biopsy, tissue extract). In a particularly preferred embodiment, the biological sample can be a cell-containing sample, more preferably a sample containing tumor cells collected from a subject to be diagnosed or treated.

Alternatively, the diagnosis can be done, by a method which allows direct quantification of antigen-specific T cells by staining with Fluorescein-labeled HLA multimeric complexes (e.g., Altman, J. D. et al., 1996, Science 274: 94; Altman, J. D. et al., 1993, Proc. Natl. Acad. Sci. USA 90:10330). Staining for intracellular lymphokines, and interferon-gamma release assays or ELISPOT assays also has been provided. Multimer staining, intracellular lymphokine staining and ELISPOT assays all appear to be at least 10-fold more sensitive than more conventional assays (Murali-Krishna, K. et al., 1998, Immunity 8: 177; Lalvani, A. et al., 1997, J. Exp. Med. 186: 859; Dunbar, P. R. et al., 1998, Curr. Biol. 8: 413). Pentamers (e.g., US 2004-209295A), dextramers (e.g., WO 02/072631), and streptamers (e.g., Nature medicine 6. 631-637 (2002)) may also be used.

Accordingly, in some embodiments, the present invention provides a method for diagnosing or evaluating an immunological response of a subject administered at least one of the SEMA5B peptides of the present invention, the method including the steps of:

(a) contacting an immunogen with immunocompetent cells under the condition suitable for induction of CTL specific to the immunogen;

(b) detecting or determining induction level of the CTL induced in step (a); and (c) correlating the immunological response of the subject with the CTL induction level.

In the context of the present invention, the immunogen is preferably includes at least one of (a) a SEMA5B peptide selected from among SEQ ID NOs: 5, 7, 27 and 34 and (b) peptides having such amino acid sequences in which such amino acid sequences have been modified with 1, 2 or more amino acid substitution(s). In the meantime, conditions suitable of induction of immunogen specific CTL are well known in the art. For example, immunocompetent cells may be cultured in vitro under the presence of immunogen(s) to induce immunogen specific CTL. In order to induce immunogen specific CTLs, any stimulating factors may be added to the cell culture. For example, IL-2 is preferable stimulating factors for the CTL induction.

In some embodiments, the step of monitoring or evaluating immunological response of a subject to be treated with peptide cancer therapy may be performed before, during and/or after the treatment. In general, during a protocol of cancer therapy, immunogenic peptides are administered repeatedly to a subject to be treated. For example, immunogenic peptides may be administered every week for 3-10 weeks. Accordingly, the immunological response of the subject can be evaluated or monitored during the cancer therapy protocol. Alternatively, the step of evaluation or monitoring of immunological response to the cancer therapy may at the completion of the therapy protocol.

According to the present invention, enhanced induction of immunogen specific CTL as compared with a control indicates that the subject to be evaluated or diagnosed immunologically responded to the immunogen(s) that has/have been administered. Suitable controls for evaluating the immunological response may include, for example, a CTL induction level when the immunocompetent cells are contacted with no peptide, or control peptide(s) having amino acid sequences other than any SEMA5B peptides. (e.g. random amino acid sequence). In a preferred embodiment, the immunological response of the subject is evaluated in a sequence specific manner, by comparison with an immunological response between each immunogen administered to the subject. In particular, even when a mixture of some kinds of SEMA5B peptides is administered to the subject, immunological response might vary depending on the peptides. In that case, by comparison of the immunological response between each peptide, peptides to which the subject show higher response can be identified.

XI. Antibodies

The present invention further provides antibodies that bind to the peptide of the present invention. Preferred antibodies specifically bind to the peptide of the present invention and will not bind (or will bind weakly) to non-peptide of the present invention. Alternatively, antibodies bind to the peptide of the invention as well as the homologs thereof. Antibodies against the peptide of the invention can find use in cancer diagnostic and prognostic assays, and imaging methodologies. Similarly, such antibodies can find use in the treatment, diagnosis, and/or prognosis of other cancers, to the extent SEMA5B is also expressed or over-expressed in a cancer patient. Moreover, intracellularly expressed antibodies (e.g., single chain antibodies) may therapeutically find use in treating cancers in which the expression of SEMA5B is involved, examples of which include, but are not limited to, esophageal cancer, NSCLC, RCC and SCLC.

The present invention also provides various immunological assay for the detection and/or quantification of SEMA5B protein (SEQ ID NO: 49) or fragments thereof including a polypeptide composed of amino acid sequences selected from among SEQ ID NOs: 5, 7, 27 and 34. Such assays may include one or more anti-SEMA5B antibodies capable of recognizing and binding a SEMA5B protein or fragments thereof, as appropriate. In the present invention, anti-SEMA5B antibodies binding to SEMA5B polypeptide preferably recognize a polypeptide composed of amino acid sequences selected from among SEQ ID NOs: 5, 7, 27 and 34. A binding specificity of antibody can be confirmed with inhibition test. That is, when the binding between an antibody to be analyzed and full-length of SEMA5B polypeptide is inhibited under presence of any fragment polypeptides having an amino acid sequence selected from among SEQ ID NOs: 5, 7, 27 and 34, the antibody specifically binds to the fragment. In the context of the present invention, such immunological assays are performed within various immunological assay formats well known in the art, including but not limited to, various types of radio-immunoassays, immuno-chromatograph technique, enzyme-linked immunosorbent assays (ELISA), enzyme-linked immunofluorescent assays (ELIFA), and the like.

Related immunological but non-antibody assays of the invention may also include T cell immunogenicity assays (inhibitory or stimulatory) as well as MHC binding assays. In addition, immunological imaging methods capable of detecting cancers expressing SEMA5B are also provided by the invention, including, but not limited to, radioscintigraphic imaging methods using labeled antibodies of the present invention. Such assays can clinically find use in the detection, monitoring, and prognosis of SEMA5B expressing cancers, examples of which include, but are not limited to, esophageal cancer, NSCLC, RCC and SCLC.

The present invention also provides antibodies that binds to a peptide of the invention. An antibody of the invention can be used in any form, such as monoclonal or polyclonal antibodies, and include antiserum obtained by immunizing an animal such as a rabbit with the peptide of the invention, all classes of polyclonal and monoclonal antibodies, human antibodies and humanized antibodies produced by genetic recombination.

A peptide of the invention used as an antigen to obtain an antibody may be derived from any animal species, but preferably is derived from a mammal such as a human, mouse, or rat, more preferably from a human. A human-derived peptide may be obtained from the nucleotide or amino acid sequences disclosed herein.

According to the present invention, the peptide to be used as an immunization antigen may be a complete protein or a partial peptide of the protein. A partial peptide may include, for example, the amino (N)-terminal or carboxy (C)-terminal fragment of a peptide of the present invention.

Herein, an antibody is defined as a protein that reacts with either the full length or a fragment of a SEMA5B peptide. In a preferred embodiment, antibody of the present invention can recognize fragment peptides of SEMA5B having an amino acid sequence selected from among SEQ ID NOs: 5, 7, 27 and 34. Methods for synthesizing oligopeptide are well known in the arts. After the synthesis, peptides may be optionally purified prior to use as immunogen. In the present invention, the oligopeptide (e.g., 9- or 10mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, but preferably the compatibility with parental cells used for cell fusion is taken into account. In general, animals of Rodentia, Lagomorpha or Primate family may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, in which a non-human animal is immunized with an antigen for preparing hybridoma, human lymphocytes such as those infected by EB virus may be immunized with a peptide, peptide expressing cells or their lysates in vitro. Then, the immunized lymphocytes are fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the peptide of the present invention is coupled. The antibody of the present invention can be used not only for purification and detection of the peptide of the present invention, but also as a candidate for agonists and antagonists of the peptide of the present invention.

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the peptides of the invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239: 1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Exemplary chromatography, with the exception of affinity includes, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the peptide of the invention, by exposing the antibody of the invention to a sample assumed to contain the peptide of the invention, and detecting or measuring the immune complex formed by the antibody and the peptide.

Because the method of detection or measurement of the peptide according to the invention can specifically detect or measure a peptide, the method can find use in a variety of experiments in which the peptide is used.

XII. Vectors and Host Cells

The present invention also provides a vector and host cell into which a nucleotide encoding the peptide of the present invention is introduced. A vector of the present invention can find use to keep a nucleotide, especially a DNA, of the present invention in host cell, to express the peptide of the present invention, or to administer the nucleotide of the present invention for gene therapy.

When E. coli is a host cell and the vector is amplified and produced in a large amount in E. coli (e.g., JM109, DH5 alpha, HB101 or XL1Blue), the vector should have "ori" to be amplified in E. coli and a marker gene for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use. For example, an expression vector to be expressed in E. coli should have the above characteristics to be amplified in E. coli. When E. coli, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the E. coli is the pelB signal sequence (Lei et al., J Bacteriol 169: 4379 (1987)). Means for introducing of the vectors into the target host cells include, for example, the calcium chloride method, and the electroporation method.

In addition to E. coli, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "Pichia Expression Kit" (Invitrogen), pNV11, SP-Q01) and expression vectors derived from Bacillus subtilis (e.g., pPL608, pKTH50) can be used for producing the polypeptide of the present invention.

In order to express the vector in animal cells, such as CHO, COS or NIH3T3 cells, the vector should carry a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Hereinafter, the present invention is described in more detail with reference to the Examples. However, while the following materials, methods and examples may serve to assist one of ordinary skill in making and using certain embodiments of the present invention, there are only intended to illustrate aspects of the present invention and thus in no way to limit the scope of the present invention. As one of ordinary skill in the art will readily recognize, methods and materials similar or equivalent to those described herein can be used in the practice or testing of the present invention.

EXAMPLES

Materials and Methods

Cell Lines

T2, HLA-A*0201-positive B-lymphoblastoid cell line, and COST, African green monkey kidney cell line, were purchased from ATCC.

Candidate Selection of Peptides Derived from SEMA5B 9-mer and 10-mer peptides derived from SEMA5B that bind to HLA-A*0201 molecule was predicted using binding prediction software "NetMHC3.0" (http://www.cbs.dtu.dk/services/NetMHC/) (Buus et al. (Tissue Antigens, 62:378-84, 2003), Nielsen et al. (Protein Sci., 12:1007-17, 2003, Bioinformatics, 20(9):1388-97, 2004)). These peptides were synthesized by Biosynthesis (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide at 20 mg/ml and stored at −80 degree C.

In vitro CTL Induction

Monocyte-derived dendritic cells (DCs) were used as antigen-presenting cells to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells isolated from a normal volunteer (HLA-A*0201 positive) by Ficoll-Paque plus (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro g/ml of each of the synthesized peptides in the presence of 3 micro g/ml of beta 2-microglobulin for 3 hr at 37 degree C. in AIM-V Medium. The generated cells appeared to express DC-associated molecules, such as CD80, CD83, CD86 and HLA class II, on their cell surfaces (data not shown). These peptide-pulsed DCs were then inactivated by X ray-irradiated (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On day 7 and 14, the T cells were further stimulated with the autologous peptide-pulsed DCs. The DCs were prepared each time by the same way described above. CTLs were tested against peptide-pulsed T2 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 December 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 micro l/well of AIM-V Medium containing 5% AS. 50 micro l/well of IL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon(IFN)-gamma enzyme-linked immunospot (ELISPOT) assay and IFN-gamma enzyme-linked immunosorbent assay (ELISA) were performed. Peptide-pulsed T2 ($1 \times 10^4$/well) was prepared as stimulator cells. Cultured cells in 48-well plate, CTL lines and CTL clones were used as responder cells. IFN-gamma ELISPOT assay and IFN-gamma ELISA assay were performed under manufacture procedure.

Establishment of the Cells Forcibly Expressing Either or Both of the Target Gene and HLA-A02

The cDNA encoding an open reading frame of target genes or HLA-A*0201 was amplified by PCR. The PCR-amplified product was cloned into expression vector. The plasmids were transfected into COS7, which is HLA-A*0201-null cell line, using lipofectamine 2000 (Invitrogen) according to the manufacturer's recommended procedures. After 2 days from transfection, the transfected cells were harvested with versene (Invitrogen) and used as the stimulator cells ($5 \times 10^4$ cells/well) for CTL activity assay.

Results

Enhanced SEMA5B Expression in Cancers

The wide gene expression profile data obtained from various cancers using cDNA-microarray revealed that SEMA5B (GenBank Accession No. NM_001031702; SEQ ID No: 48) expression was elevated. SEMA5B expression was validly elevated in 1 out of 2 Esophageal Cancers, 1 out of 1 NSCLC, 14 out of 17 RCC and 4 out of 4 SCLC, as compared with corresponding normal tissue (Table 1).

TABLE 1

Ratio of cases observed up-regulation of SEMA5B in cancerous tissue as compared with normal corresponding tissue.

| Cancer/Tumor | Ratio |
| --- | --- |
| Esophageal Cancer | 1/2 |
| NSCLC | 1/1 |
| RCC | 14/17 |
| SCLC | 4/4 |

Prediction of HLA-A02 Binding Peptides Derived from SEMA5B

Tables 2a and 2b show the HLA-A02 binding 9mer and 10mer peptides of SEMA5B in the order of high binding affinity. A total of 47 peptides with potential HLA-A02 binding ability were selected and examined to determine the epitope peptides.

TABLE 2a

HLA-A02 binding 9 mer peptides derived from SEMA5B

| Start Position | Amino acid sequence | Kd (nM) | SEQ ID NO |
| --- | --- | --- | --- |
| 330 | FLLEDTWTT | 8 | 1 |
| 450 | LMSEAVQPV | 9 | 2 |
| 69 | LLLPSLTLL | 13 | 3 |
| 1045 | FLGSGLLTL | 14 | 4 |
| 70 | LLPSLTLLV | 17 | 5 |
| 287 | FVAAYDIGL | 17 | 6 |
| 1049 | GLLTLAVYL | 18 | 7 |
| 59 | MVLAGPLAV | 19 | 8 |
| 447 | RLFLMSEAV | 28 | 9 |
| 592 | SLWTQNITA | 41 | 10 |
| 281 | WLNEPNFVA | 86 | 11 |
| 52 | RTAEGPIMV | 87 | 12 |
| 543 | GLRDGVLRV | 90 | 13 |
| 24 | QQLRCGWTV | 91 | 14 |
| 35 | WLLSLVRGL | 99 | 15 |
| 313 | TVYSRVARV | 99 | 16 |
| 155 | SLLQATEWA | 103 | 17 |

TABLE 2a-continued

HLA-A02 binding 9 mer peptides derived from SEMA5B

| Start Position | Amino acid sequence | Kd (nM) | SEQ ID NO |
|---|---|---|---|
| 648 | GLDCLGPAI | 113 | 18 |
| 68 | SLLLPSLTL | 154 | 19 |
| 218 | RTIEKINGV | 165 | 20 |
| 43 | LLPCLPPGA | 204 | 21 |
| 148 | RLSLANVSL | 233 | 22 |
| 31 | TVGGWLLSL | 311 | 23 |
| 590 | NMSLWTQNI | 373 | 24 |

TABLE 2b

HLA-A02 binding 10 mer peptides derived from SEMA5B

| Start Position | Amino acid sequence | Kd (nM) | SEQ ID NO |
|---|---|---|---|
| 449 | FLMSEAVQPV | 5 | 25 |
| 145 | YLFRLSLANV | 8 | 26 |
| 69 | LLLPSLTLLV | 13 | 27 |
| 1045 | FLGSGLLTLA | 31 | 28 |
| 58 | IMVLAGPLAV | 38 | 29 |
| 533 | ILHSARALFV | 47 | 30 |
| 42 | GLLPCLPPGA | 49 | 31 |
| 68 | SLLLPSLTLL | 67 | 32 |
| 508 | SLHGCYLEEL | 75 | 33 |
| 370 | LIYGVFTTNV | 103 | 34 |
| 539 | ALFVGLRDGV | 113 | 35 |
| 38 | SLVRGLLPCL | 144 | 36 |
| 441 | SLQDAQRLFL | 158 | 37 |
| 35 | WLLSLVRGLL | 191 | 38 |
| 484 | TLYHVLYIGT | 353 | 39 |
| 137 | QLIVGARNYL | 416 | 40 |
| 148 | RLSLANVSLL | 446 | 41 |
| 479 | VQAKDTLYHV | 525 | 42 |
| 243 | SQGELYAATV | 531 | 43 |
| 106 | VAFEDLQPWV | 614 | 44 |
| 60 | VLAGPLAVSL | 788 | 45 |
| 281 | WLNEPNFVAA | 1908 | 46 |
| 592 | SLWTQNITAC | 7017 | 47 |

Start position indicates the number of amino acid residue from the N-terminus of SEMA5B. Binding dissociation constant [Kd (nM)] are derived from "NetMHC3.0".

CTL Induction with the Predicted Peptides from SEMA5B Restricted with HLA-A*0201

Figure 1:
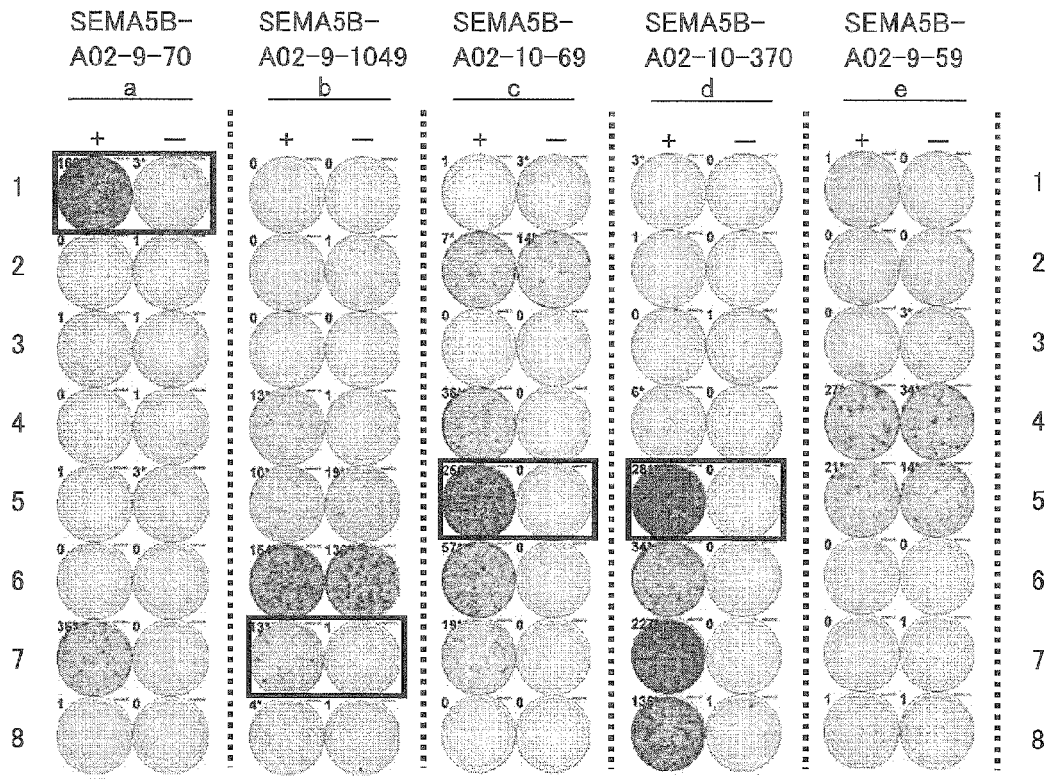
FIG. 1 is composed of a series of photographs, (a) to (e), depicting the results of IFN-gamma ELISPOT assays on CTLs that were induced with peptides derived from SEMA5B. The CTLs in well number #1 stimulated with SEMA5B-A02-9-70 (SEQ ID NO: 5) (a), in #7 stimulated with SEMA5B-A02-9-1049 (SEQ ID NO: 7) (b), in #5 stimulated with SEMA5B-A02-10-69 (SEQ ID NO: 27) (c) and in #5 stimulated with SEMA5B-A02-10-370 (SEQ ID NO: 34) (d) showed potent IFN-gamma production compared with the control, respectively. The square on the well of these pictures indicates that the cells from corresponding well were expanded to establish CTL lines. In contrast, as typical case of negative data, specific IFN-gamma production from the CTL stimulated with SEMA5B-A02-9-59 (SEQ ID NO: 8) (e) was not shown. In the figures, "+" indicates the IFN-gamma production against target cells pulsed with the appropriate peptide, and "−" indicates the IFN-gamma production against target cells not pulsed with any peptides.

CTLs for those peptides derived from SEMA5B were generated according to the protocols as described in "Materials and Methods". Peptide-specific CTL activity was detected by IFN-gamma ELISPOT assay (FIG. 1). It showed that the well number #1 stimulated with SEMA5B-A02-9-70 (SEQ ID NO: 5) (a), #7 stimulated with SEMA5B-A02-9-1049 (SEQ ID NO: 7) (b), #5 stimulated with SEMA5B-A02-10-69 (SEQ ID NO: 27) (c) and #5 stimulated with SEMA5B-A02-10-370 (SEQ ID NO: 34) (d) demonstrated potent IFN-gamma production as compared to the control wells. On the other hand, no specific CTL activity was detected by stimulation with other peptides shown in Table 2a and 2b, despite those peptides had possible binding activity with HLA-A*0201. As a typical case of negative data, it was not shown specific IFN-gamma production from the CTL stimulated with SEMA5B-A02-9-59 (SEQ ID NO: 8) (e). As a result, it indicated that 4 peptides derived from SEMA5B were selected as the peptides that could induce potent CTLs.

Establishment of CTL Line and Clone Against SEMA5B Derived Peptide

Figure 2:
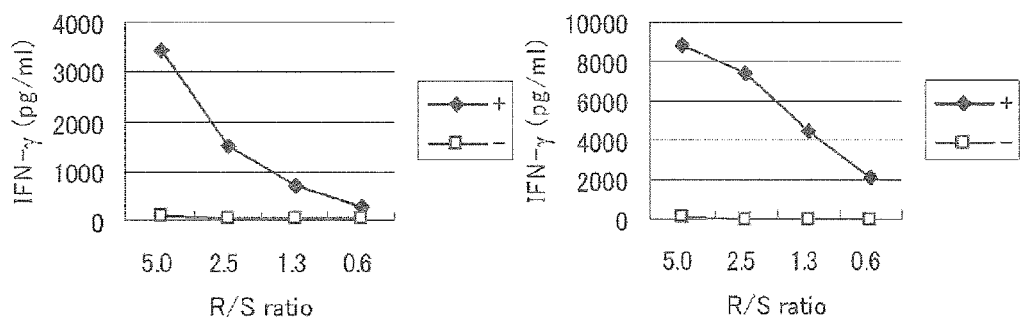
FIG. 2 is composed of a series of line graphs, (a) to (c), depicting the results of an IFN-gamma ELISA assay demonstrating the IFN-gamma production of CTL lines stimulated with (a) SEMA5B-A02-9-70 (SEQ ID NO: 5), (b) SEMA5B-
Figure 2:
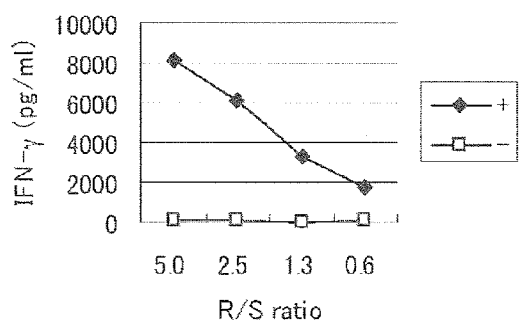

The cells in the well number #1 stimulated with SEMA5B-A02-9-70 (SEQ ID NO: 5) (a), #5 stimulated with SEMA5B-A02-10-69 (SEQ ID NO: 27) (b) and #5 stimulated with SEMA5B-A02-10-370 (SEQ ID NO: 34) (c), which showed peptide-specific CTL activity in IFN-gamma ELISPOT assay, were expanded and established the CTL lines. CTL activity of these CTL lines was measured by IFN-gamma ELISA (FIG. 2). It demonstrated that the CTL lines showed potent IFN-gamma production against the target cells pulsed with the corresponding peptide as compared to target cells without peptide pulse. Furthermore, the CTL clones were established by limiting dilution from the CTL lines as described in "Materials and Methods", and IFN-gamma production from the CTL clones against target cells pulsed with each peptide was measured by IFN-gamma ELISA. Potent IFN-gamma production was observed from the CTL clones stimulated with SEMA5B-A02-9-70 (SEQ ID NO: 5) (a), SEMA5B-A02-10-69 (SEQ ID NO: 27) (b) or SEMA5B-A02-10-370 (SEQ ID NO: 34) (c) (FIG. 3).

Specific CTL Activity Against Target Cells Expressing SEMA5B and HLA-A*0201

The established CTL line raised against SEMA5B-A02-10-69 (SEQ ID NO: 27) peptide was examined for the ability to recognize target cells that express SEMA5B and HLA-A*0201 molecule. COS7 cells transfected with both the full length of SEMA5B and HLA-A*0201 gene (a specific model for the target cells that express SEMA5B and HLA-A*0201 gene) were prepared as stimulator cells, and COS7 cells transfected with either full length of SEMA5B or HLA-A* 0201 were used as the controls. In FIG. 4, the CTL line stimulated with SEMA5B-A02-10-69 (SEQ ID NO: 27) showed potent CTL activity against COS7 cells expressing both SEMA5B and HLA-A*0201. On the other hand, no significant specific CTL activity was detected against the controls. Thus, these data clearly demonstrate that SEMA5B-A02-10-69 (SEQ ID NO: 27) peptide is endogenously processed and expressed on the target cells with HLA-A*0201 molecule and is recognized by the CTLs. These results indicate that this peptide derived from SEMA5B may be available to apply the cancer vaccines for patients with SEMA5B expressing tumors.

Homology Analysis of Antigen Peptides

The CTLs stimulated with SEMA5B-A02-9-70 (SEQ ID NO: 5), SEMA5B-A02-9-1049 (SEQ ID NO: 7), SEMA5B-A02-10-69 (SEQ ID NO: 27) and SEMA5B-A02-10-370 (SEQ ID NO: 34) showed significant and specific CTL activity. This result may be due to the fact that the sequence of SEMA5B-A02-9-70 (SEQ ID NO: 5), SEMA5B-A02-9-1049 (SEQ ID NO: 7), SEMA5B-A02-10-69 (SEQ ID NO: 27) and SEMA5B-A02-10-370 (SEQ ID NO: 34) are homologous to peptide derived from other molecules that are known to sensitize the human immune system. To exclude this possibility, homology analyses were performed for these peptide sequences using as queries the BLAST algorithm (http://www.ncbi.nlm.nih.gov/blast/blast.cgi) which revealed no sequence with significant homology. The results of homology analysis indicate that the sequence of SEMA5B-A02-9-70 (SEQ ID NO: 5), SEMA5B-A02-9-1049 (SEQ ID NO: 7), SEMA5B-A02-10-69 (SEQ ID NO: 27) and SEMA5B-A02-10-370 (SEQ ID NO: 34) are unique and thus, there is little possibility, to our best knowledge, that this molecules raise unintended immunologic response to some unrelated molecule.

INDUSTRIAL APPLICABILITY

The present invention provides new TAAs, particularly those derived from SEMA5B that may induce potent and specific anti-tumor immune responses and have applicability to a wide variety of cancer types. Such TAAs can find use as peptide vaccines against diseases associated with SEMA5B, e.g., cancer, more particularly, esophageal cancer, NSCLC, RCC and SCLC.

While the present invention is herein described in detail and with reference to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. An isolated peptide of less than 14 amino acids that (i) comprises an amino acid sequence of SEQ ID NO: 27 in which 1 or 2 amino acid(s) are substituted, deleted, inserted, and/or added and (ii) retains the cytotoxic T lymphocyte (CTL) inducibility of the original peptide.

2. The isolated peptide of claim 1, wherein the isolated peptide has one or both of the following characteristics:

(a) the second amino acid from the N-terminus of the amino acid sequence of SEQ ID NO: 27 is selected from the group consisting of leucine and methionine; and (b) the C-terminal amino acid of the amino acid sequence of SEQ ID NO: 27 is selected from the group consisting of valine and leucine.

3. The isolated peptide of claim 1, wherein said peptide is a nonapeptide or decapeptide.

4. A composition for inducing a CTL, wherein the composition comprises (a) one or more peptide(s) of less than 15 amino acid and comprising the amino acid sequence of SEQ ID NO: 27, or (b) one or more peptide(s) of claim 1, wherein the composition further comprises a carrier selected from the group consisting of sterilized water, physiological saline and phosphate buffer.

5. A pharmaceutical composition comprising (a) one or more peptide s of less than 15 amino acid and comprising the amino acid sequence of SEQ ID NO: 27, or (b) one or more peptide(s) of claim 1, as an active ingredient, wherein the pharmaceutical composition further comprises a carrier selected from the group consisting of sterilized water, physiological saline and phosphate buffer.

6. A method for inducing an antigen-presenting cell (APC) having CTL inducibility, said method comprising a step
of contacting an APC with (a) a peptide of less than 15 amino acid and comprising the amino acid sequence of SEQ ID NO: 27, or (b) the peptide of claim 1 in vitro, or ex vivo.

7. A method for inducing a CTL, said method comprising a step
of co-culturing a CD8 positive T cell with an APC that presents on its surface a complex of an HLA antigen and (a) a peptide of less than 15 amino acid and comprising the amino acid sequence of SEQ ID NO: 27, or (b) the peptide of claim 1.

* * * * *

SEQUENCE LISTING

```
<160> NUMBER OF SEQ ID NOS: 53

<210> SEQ ID NO 1
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 1

Phe Leu Leu Glu Asp Thr Trp Thr Thr
1               5

<210> SEQ ID NO 2
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 2

Leu Met Ser Glu Ala Val Gln Pro Val
1               5

<210> SEQ ID NO 3
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 3

Leu Leu Leu Pro Ser Leu Thr Leu Leu
1               5

<210> SEQ ID NO 4
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 4

Phe Leu Gly Ser Gly Leu Leu Thr Leu
1               5

<210> SEQ ID NO 5
<211> LENGTH: 9
<212> TYPE: PRT
```

```
<213> ORGANISM: Artificial Sequence
<220> FEATURE:
<223> OTHER INFORMATION: An artificially synthesized peptide sequence

<400> SEQUENCE: 5

Leu Leu Pro Ser Leu Thr Leu Leu Val
1               5

<210> SEQ ID NO 6
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 6

Phe Val Ala Ala Tyr Asp Ile Gly Leu
1               5

<210> SEQ ID NO 7
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 7

Gly Leu Leu Thr Leu Ala Val Tyr Leu
1               5

<210> SEQ ID NO 8
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 8

Met Val Leu Ala Gly Pro Leu Ala Val
1               5

<210> SEQ ID NO 9
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 9

Arg Leu Phe Leu Met Ser Glu Ala Val
1               5

<210> SEQ ID NO 10
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 10

Ser Leu Trp Thr Gln Asn Ile Thr Ala
1               5

<210> SEQ ID NO 11
<211> LENGTH: 9
<212> TYPE: PRT
<213> ORGANISM: Artificial Sequence
```

```
<220> FEATURE:
<223> OTHER INFORMATION: An artificially synthesized peptide sequence

<400> SEQUENCE: 11

Trp Leu Asn Glu Pro Asn Phe Val Ala
1               5

<210> SEQ ID NO 12
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 12

Arg Thr Ala Glu Gly Pro Ile Met Val
1               5

<210> SEQ ID NO 13
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 13

Gly Leu Arg Asp Gly Val Leu Arg Val
1               5

<210> SEQ ID NO 14
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 14

Gln Gln Leu Arg Cys Gly Trp Thr Val
1               5

<210> SEQ ID NO 15
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 15

Trp Leu Leu Ser Leu Val Arg Gly Leu
1               5

<210> SEQ ID NO 16
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 16

Thr Val Tyr Ser Arg Val Ala Arg Val
1               5

<210> SEQ ID NO 17
<211> LENGTH: 9
<212> TYPE: PRT
<213> ORGANISM: Artificial Sequence
<220> FEATURE:
```

```
<223> OTHER INFORMATION: An artificially synthesized peptide sequence

<400> SEQUENCE: 17

Ser Leu Leu Gln Ala Thr Glu Trp Ala
1               5

<210> SEQ ID NO 18
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 18

Gly Leu Asp Cys Leu Gly Pro Ala Ile
1               5

<210> SEQ ID NO 19
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 19

Ser Leu Leu Leu Pro Ser Leu Thr Leu
1               5

<210> SEQ ID NO 20
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 20

Arg Thr Ile Glu Lys Ile Asn Gly Val
1               5

<210> SEQ ID NO 21
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 21

Leu Leu Pro Cys Leu Pro Pro Gly Ala
1               5

<210> SEQ ID NO 22
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 22

Arg Leu Ser Leu Ala Asn Val Ser Leu
1               5

<210> SEQ ID NO 23
<211> LENGTH: 9
<212> TYPE: PRT
<213> ORGANISM: Artificial Sequence
<220> FEATURE:
<223> OTHER INFORMATION: An artificially synthesized peptide sequence
```

```
<400> SEQUENCE: 23

Thr Val Gly Gly Trp Leu Leu Ser Leu
1               5

<210> SEQ ID NO 24
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 24

Asn Met Ser Leu Trp Thr Gln Asn Ile
1               5

<210> SEQ ID NO 25
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 25

Phe Leu Met Ser Glu Ala Val Gln Pro Val
1               5                   10

<210> SEQ ID NO 26
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 26

Tyr Leu Phe Arg Leu Ser Leu Ala Asn Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 27

Leu Leu Leu Pro Ser Leu Thr Leu Leu Val
1               5                   10

<210> SEQ ID NO 28
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 28

Phe Leu Gly Ser Gly Leu Leu Thr Leu Ala
1               5                   10

<210> SEQ ID NO 29
<211> LENGTH: 10
<212> TYPE: PRT
<213> ORGANISM: Artificial Sequence
<220> FEATURE:
<223> OTHER INFORMATION: An artificially synthesized peptide sequence
```

<400> SEQUENCE: 29

Ile Met Val Leu Ala Gly Pro Leu Ala Val
1               5                   10

<210> SEQ ID NO 30
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 30

Ile Leu His Ser Ala Arg Ala Leu Phe Val
1               5                   10

<210> SEQ ID NO 31
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 31

Gly Leu Leu Pro Cys Leu Pro Pro Gly Ala
1               5                   10

<210> SEQ ID NO 32
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 32

Ser Leu Leu Leu Pro Ser Leu Thr Leu Leu
1               5                   10

<210> SEQ ID NO 33
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 33

Ser Leu His Gly Cys Tyr Leu Glu Glu Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 34

Leu Ile Tyr Gly Val Phe Thr Thr Asn Val
1               5                   10

<210> SEQ ID NO 35
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 35

```
Ala Leu Phe Val Gly Leu Arg Asp Gly Val
1               5                   10

<210> SEQ ID NO 36
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 36

Ser Leu Val Arg Gly Leu Leu Pro Cys Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 37

Ser Leu Gln Asp Ala Gln Arg Leu Phe Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 38

Trp Leu Leu Ser Leu Val Arg Gly Leu Leu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 39

Thr Leu Tyr His Val Leu Tyr Ile Gly Thr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 40

Gln Leu Ile Val Gly Ala Arg Asn Tyr Leu
1               5                   10

<210> SEQ ID NO 41
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 41
```

Arg Leu Ser Leu Ala Asn Val Ser Leu Leu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 42

Val Gln Ala Lys Asp Thr Leu Tyr His Val
1               5                   10

<210> SEQ ID NO 43
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 43

Ser Gln Gly Glu Leu Tyr Ala Ala Thr Val
1               5                   10

<210> SEQ ID NO 44
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 44

Val Ala Phe Glu Asp Leu Gln Pro Trp Val
1               5                   10

<210> SEQ ID NO 45
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 45

Val Leu Ala Gly Pro Leu Ala Val Ser Leu
1               5                   10

<210> SEQ ID NO 46
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 46

Trp Leu Asn Glu Pro Asn Phe Val Ala Ala
1               5                   10

<210> SEQ ID NO 47
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 47

Ser Leu Trp Thr Gln Asn Ile Thr Ala Cys

<210> SEQ ID NO 48
<211> LENGTH: 4737
<212> TYPE: DNA
<213> ORGANISM: Homo sapiens
<220> FEATURE:
<221> NAME/KEY: CDS
<222> LOCATION: (305)..(3760)

<400> SEQUENCE: 48

```
agttggagcg cggggggttgg tgccagagcc cagctccgcc gagccgggcg ggtcggcagc      60
gcatccagcg gctgctggga gcccgagcgc agcgggcgcg ggcccgggtg gggactgcac     120
cggagcgctg agagctggag gccgttcctg cgcggccgcc ccattcccag accggccgcc     180
agcccatctg gttagctccc gccgctccgc gccgcccggg agtcgggagc gcgggggaac     240
cgggcacctg cacccgcctc tgggagtgag tggttccagc tggtgcctgg cctgtgtctc     300
```

```
ttgg atg ccc tgt ggc ttc agt ccg tct cct gtt gcc cac cac ctc gtc      349
     Met Pro Cys Gly Phe Ser Pro Ser Pro Val Ala His His Leu Val
      1               5                  10                  15 cct ggg ccg cct gat acc cca gcc caa cag cta agg tgt gga tgg aca       397
Pro Gly Pro Pro Asp Thr Pro Ala Gln Gln Leu Arg Cys Gly Trp Thr
                 20                  25                  30 gta ggg ggc tgg ctt ctc tca ctg gtc agg ggt ctt ctc ccc tgt ctg       445
Val Gly Gly Trp Leu Leu Ser Leu Val Arg Gly Leu Leu Pro Cys Leu
         35                  40                  45 cct ccc gga gct agg act gca gag ggg cct atc atg gtg ctt gca ggc       493
Pro Pro Gly Ala Arg Thr Ala Glu Gly Pro Ile Met Val Leu Ala Gly
     50                  55                  60 ccc ctg gct gtc tcg ctg ttg ctg ccc agc ctc aca ctg ctg gtg tcc       541
Pro Leu Ala Val Ser Leu Leu Leu Pro Ser Leu Thr Leu Leu Val Ser
 65                  70                  75 cac ctc tcc agc tcc cag gat gtc tcc agt gag ccc agc agt gag cag       589
His Leu Ser Ser Ser Gln Asp Val Ser Ser Glu Pro Ser Ser Glu Gln
 80                  85                  90                  95 cag ctg tgc gcc ctt agc aag cac ccc acc gtg gcc ttt gaa gac ctg       637
Gln Leu Cys Ala Leu Ser Lys His Pro Thr Val Ala Phe Glu Asp Leu
                100                 105                 110 cag ccg tgg gtc tct aac ttc acc tac cct gga gcc cgg gat ttc tcc       685
Gln Pro Trp Val Ser Asn Phe Thr Tyr Pro Gly Ala Arg Asp Phe Ser
             115                 120                 125 cag ctg gct ttg gac ccc tcc ggg aac cag ctc atc gtg gga gcc agg       733
Gln Leu Ala Leu Asp Pro Ser Gly Asn Gln Leu Ile Val Gly Ala Arg
         130                 135                 140 aac tac ctc ttc aga ctc agc ctt gcc aat gtc tct ctt ctt cag gcc       781
Asn Tyr Leu Phe Arg Leu Ser Leu Ala Asn Val Ser Leu Leu Gln Ala
     145                 150                 155 aca gag tgg gcc tcc agt gag gac acg cgc cgc tcc tgc caa agc aaa       829
Thr Glu Trp Ala Ser Ser Glu Asp Thr Arg Arg Ser Cys Gln Ser Lys
160                 165                 170                 175 ggg aag act gag gag gag tgt cag aac tac gtg cga gtc ctg atc gtc       877
Gly Lys Thr Glu Glu Glu Cys Gln Asn Tyr Val Arg Val Leu Ile Val
                180                 185                 190 gcc ggc cgg aag gtg ttc atg tgt gga acc aat gcc ttt tcc ccc atg       925
Ala Gly Arg Lys Val Phe Met Cys Gly Thr Asn Ala Phe Ser Pro Met
             195                 200                 205 tgc acc agc aga cag gtg ggg aac ctc agc cgg act att gag aag atc       973
Cys Thr Ser Arg Gln Val Gly Asn Leu Ser Arg Thr Ile Glu Lys Ile
         210                 215                 220
```

```
aat ggt gtg gcc cgc tgc ccc tat gac cca cgc cac aac tcc aca gct      1021
Asn Gly Val Ala Arg Cys Pro Tyr Asp Pro Arg His Asn Ser Thr Ala
    225                 230                 235 gtc atc tcc tcc cag ggg gag ctc tat gca gcc acg gtc atc gac ttc      1069
Val Ile Ser Ser Gln Gly Glu Leu Tyr Ala Ala Thr Val Ile Asp Phe
240                 245                 250                 255 tca ggt cgg gac cct gcc atc tac cgc agc ctg ggc agt ggg cca ccg      1117
Ser Gly Arg Asp Pro Ala Ile Tyr Arg Ser Leu Gly Ser Gly Pro Pro
                260                 265                 270 ctt cgc act gcc caa tat aac tcc aag tgg ctt aat gag cca aac ttc      1165
Leu Arg Thr Ala Gln Tyr Asn Ser Lys Trp Leu Asn Glu Pro Asn Phe
            275                 280                 285 gtg gca gcc tat gat att ggg ctg ttt gca tac ttc ttc ctg cgg gag      1213
Val Ala Ala Tyr Asp Ile Gly Leu Phe Ala Tyr Phe Phe Leu Arg Glu
        290                 295                 300 aac gca gtg gag cac gac tgt gga cgc acc gtg tac tct cgc gtg gcc      1261
Asn Ala Val Glu His Asp Cys Gly Arg Thr Val Tyr Ser Arg Val Ala
    305                 310                 315 cgc gtg tgc aag aat gac gtg ggg ggc cga ttc ctg ctg gag gac aca      1309
Arg Val Cys Lys Asn Asp Val Gly Gly Arg Phe Leu Leu Glu Asp Thr
320                 325                 330                 335 tgg acc aca ttc atg aag gcc cgg ctc aac tgc tcc cgc ccg ggc gag      1357
Trp Thr Thr Phe Met Lys Ala Arg Leu Asn Cys Ser Arg Pro Gly Glu
                340                 345                 350 gtc ccc ttc tac tat aac gag ctg cag agt gcc ttc cac ttg ccg gag      1405
Val Pro Phe Tyr Tyr Asn Glu Leu Gln Ser Ala Phe His Leu Pro Glu
            355                 360                 365 cag gac ctc atc tat gga gtt ttc aca acc aac gta aac agc atc gcg      1453
Gln Asp Leu Ile Tyr Gly Val Phe Thr Thr Asn Val Asn Ser Ile Ala
        370                 375                 380 gct tct gct gtc tgc gcc ttc aac ctc agt gct atc tcc cag gct ttc      1501
Ala Ser Ala Val Cys Ala Phe Asn Leu Ser Ala Ile Ser Gln Ala Phe
    385                 390                 395 aat ggc cca ttt cgc tac cag gag aac ccc agg gct gcc tgg ctc ccc      1549
Asn Gly Pro Phe Arg Tyr Gln Glu Asn Pro Arg Ala Ala Trp Leu Pro
400                 405                 410                 415 ata gcc aac ccc atc ccc aat ttc cag tgt ggc acc ctg cct gag acc      1597
Ile Ala Asn Pro Ile Pro Asn Phe Gln Cys Gly Thr Leu Pro Glu Thr
                420                 425                 430 ggt ccc aac gag aac ctg acg gag cgc agc ctg cag gac gcg cag cgc      1645
Gly Pro Asn Glu Asn Leu Thr Glu Arg Ser Leu Gln Asp Ala Gln Arg
            435                 440                 445 ctc ttc ctg atg agc gag gcc gtg cag ccg gtg aca ccc gag ccc tgt      1693
Leu Phe Leu Met Ser Glu Ala Val Gln Pro Val Thr Pro Glu Pro Cys
        450                 455                 460 gtc acc cag gac agc gtg cgc ttc tca cac ctc gtg gtg gac ctg gtg      1741
Val Thr Gln Asp Ser Val Arg Phe Ser His Leu Val Val Asp Leu Val
    465                 470                 475 cag gct aaa gac acg ctc tac cat gta ctc tac att ggc acc gag tcg      1789
Gln Ala Lys Asp Thr Leu Tyr His Val Leu Tyr Ile Gly Thr Glu Ser
480                 485                 490                 495 ggc acc atc ctg aag gcg ctg tcc acg gcg agc cgc agc ctc cac ggc      1837
Gly Thr Ile Leu Lys Ala Leu Ser Thr Ala Ser Arg Ser Leu His Gly
                500                 505                 510 tgc tac ctg gag gag ctg cac gtg ctg ccc ccc ggg cgc cgc gag ccc      1885
Cys Tyr Leu Glu Glu Leu His Val Leu Pro Pro Gly Arg Arg Glu Pro
            515                 520                 525 ctg cgc agc ctg cgc atc ctg cac agc gcc cgc gcg ctc ttc gtg ggg      1933
Leu Arg Ser Leu Arg Ile Leu His Ser Ala Arg Ala Leu Phe Val Gly
        530                 535                 540
```

-continued

| | | |
|---|---|---|
| ctg aga gac ggc gtc ctg cgg gtc cca ctg gag agg tgc gcc gcc tac<br>Leu Arg Asp Gly Val Leu Arg Val Pro Leu Glu Arg Cys Ala Ala Tyr<br>545                      550                      555 | 1981 |
| cgc agc cag ggg gca tgc ctg ggg gcc cgg gac ccg tac tgt ggc tgg<br>Arg Ser Gln Gly Ala Cys Leu Gly Ala Arg Asp Pro Tyr Cys Gly Trp<br>560                      565                      570                      575 | 2029 |
| gac ggg aag cag caa cgt tgc agc aca ctc gag gac agc tcc aac atg<br>Asp Gly Lys Gln Gln Arg Cys Ser Thr Leu Glu Asp Ser Ser Asn Met<br>                580                      585                      590 | 2077 |
| agc ctc tgg acc cag aac atc acc gcc tgt cct gtg cgg aat gtg aca<br>Ser Leu Trp Thr Gln Asn Ile Thr Ala Cys Pro Val Arg Asn Val Thr<br>          595                      600                      605 | 2125 |
| cgg gat ggg ggc ttc ggc cca tgg tca cca tgg caa cca tgt gag cac<br>Arg Asp Gly Gly Phe Gly Pro Trp Ser Pro Trp Gln Pro Cys Glu His<br>610                      615                      620 | 2173 |
| ttg gat ggg gac aac tca ggc tct tgc ctg tgt cga gct cga tcc tgt<br>Leu Asp Gly Asp Asn Ser Gly Ser Cys Leu Cys Arg Ala Arg Ser Cys<br>625                      630                      635 | 2221 |
| gat tcc cct cga ccc cgc tgt ggg ggc ctt gac tgc ctg ggg cca gcc<br>Asp Ser Pro Arg Pro Arg Cys Gly Gly Leu Asp Cys Leu Gly Pro Ala<br>640                      645                      650                      655 | 2269 |
| atc cac atc gcc aac tgc tcc agg aat ggg gcg tgg acc ccg tgg tca<br>Ile His Ile Ala Asn Cys Ser Arg Asn Gly Ala Trp Thr Pro Trp Ser<br>                660                      665                      670 | 2317 |
| tcg tgg gcg ctg tgc agc acg tcc tgt ggc atc ggc ttc cag gtc cgc<br>Ser Trp Ala Leu Cys Ser Thr Ser Cys Gly Ile Gly Phe Gln Val Arg<br>          675                      680                      685 | 2365 |
| cag cga agt tgc agc aac cct gct ccc cgc cac ggg ggc cgc atc tgc<br>Gln Arg Ser Cys Ser Asn Pro Ala Pro Arg His Gly Gly Arg Ile Cys<br>690                      695                      700 | 2413 |
| gtg ggc aag agc cgg gag gaa cgg ttc tgt aat gag aac acg cct tgc<br>Val Gly Lys Ser Arg Glu Glu Arg Phe Cys Asn Glu Asn Thr Pro Cys<br>705                      710                      715 | 2461 |
| ccg gtg ccc atc ttc tgg gct tcc tgg ggc tcc tgg agc aag tgc agc<br>Pro Val Pro Ile Phe Trp Ala Ser Trp Gly Ser Trp Ser Lys Cys Ser<br>720                      725                      730                      735 | 2509 |
| agc aac tgt gga ggg ggc atg cag tcg cgg cgt cgg gcc tgc gag aac<br>Ser Asn Cys Gly Gly Gly Met Gln Ser Arg Arg Arg Ala Cys Glu Asn<br>                740                      745                      750 | 2557 |
| ggc aac tcc tgc ctg ggc tgc ggc gtg gag ttc aag acg tgc aac ccc<br>Gly Asn Ser Cys Leu Gly Cys Gly Val Glu Phe Lys Thr Cys Asn Pro<br>          755                      760                      765 | 2605 |
| gag ggc tgc ccc gaa gtg cgg cgc aac acc ccc tgg acg ccg tgg ctg<br>Glu Gly Cys Pro Glu Val Arg Arg Asn Thr Pro Trp Thr Pro Trp Leu<br>770                      775                      780 | 2653 |
| ccc gtg aac gtg acg cag ggc ggg gca cgg cag gag cag cgg ttc cgc<br>Pro Val Asn Val Thr Gln Gly Gly Ala Arg Gln Glu Gln Arg Phe Arg<br>785                      790                      795 | 2701 |
| ttc acc tgc cgc gcg ccc ctt gca gac ccg cac ggc ctg cag ttc ggc<br>Phe Thr Cys Arg Ala Pro Leu Ala Asp Pro His Gly Leu Gln Phe Gly<br>800                      805                      810                      815 | 2749 |
| agg aga agg acc gag acg agg acc tgt ccc gcg gac ggc tcc ggc tcc<br>Arg Arg Arg Thr Glu Thr Arg Thr Cys Pro Ala Asp Gly Ser Gly Ser<br>                820                      825                      830 | 2797 |
| tgc gac acc gac gcc ctg gtg gag gtc ctc ctg cgc agc ggg agc acc<br>Cys Asp Thr Asp Ala Leu Val Glu Val Leu Leu Arg Ser Gly Ser Thr<br>          835                      840                      845 | 2845 |
| tcc ccg cac acg gtg agc ggg ggc tgg gcc gcc tgg ggc ccg tgg tcg<br>Ser Pro His Thr Val Ser Gly Gly Trp Ala Ala Trp Gly Pro Trp Ser | 2893 |

```
                850                 855                 860
tcc tgc tcc cgg gac tgc gag ctg ggc ttc cgc gtc cgc aag aga acg    2941
Ser Cys Ser Arg Asp Cys Glu Leu Gly Phe Arg Val Arg Lys Arg Thr
865                 870                 875 tgc act aac ccg gag ccc cgc aac ggg ggc ctg ccc tgc gtg ggc gat    2989
Cys Thr Asn Pro Glu Pro Arg Asn Gly Gly Leu Pro Cys Val Gly Asp
880                 885                 890                 895 gct gcc gag tac cag gac tgc aac ccc cag gct tgc cca gtt cgg ggt    3037
Ala Ala Glu Tyr Gln Asp Cys Asn Pro Gln Ala Cys Pro Val Arg Gly
                900                 905                 910 gct tgg tcc tgc tgg acc tca tgg tct cca tgc tca gct tcc tgt ggt    3085
Ala Trp Ser Cys Trp Thr Ser Trp Ser Pro Cys Ser Ala Ser Cys Gly
            915                 920                 925 ggg ggt cac tat caa cgc acc cgt tcc tgc acc agc ccc gca ccc tcc    3133
Gly Gly His Tyr Gln Arg Thr Arg Ser Cys Thr Ser Pro Ala Pro Ser
        930                 935                 940 cca ggt gag gac atc tgt ctc ggg ctg cac acg gag gag gca cta tgt    3181
Pro Gly Glu Asp Ile Cys Leu Gly Leu His Thr Glu Glu Ala Leu Cys
    945                 950                 955 gcc aca cag gcc tgc cca gaa ggc tgg tcg ccc tgg tct gag tgg agt    3229
Ala Thr Gln Ala Cys Pro Glu Gly Trp Ser Pro Trp Ser Glu Trp Ser
960                 965                 970                 975 aag tgc act gac gac gga gcc cag agc cga agc cgg cac tgt gag gag    3277
Lys Cys Thr Asp Asp Gly Ala Gln Ser Arg Ser Arg His Cys Glu Glu
                980                 985                 990 ctc ctc cca ggg tcc agc gcc tgt gct gga aac agc agc cag agc cgc    3325
Leu Leu Pro Gly Ser Ser Ala Cys Ala Gly Asn Ser Ser Gln Ser Arg
            995                 1000                1005 ccc tgc ccc tac agc gag att ccc gtc atc ctg cca gcc tcc agc        3370
Pro Cys Pro Tyr Ser Glu Ile Pro Val Ile Leu Pro Ala Ser Ser
        1010                1015                1020 atg gag gag gcc acc gac tgt gca ggg ttc aat ctc atc cac ttg        3415
Met Glu Glu Ala Thr Asp Cys Ala Gly Phe Asn Leu Ile His Leu
    1025                1030                1035 gtg gcc acg ggc atc tcc tgc ttc ttg ggc tct ggg ctc ctg acc        3460
Val Ala Thr Gly Ile Ser Cys Phe Leu Gly Ser Gly Leu Leu Thr
1040                1045                1050 cta gca gtg tac ctg tct tgc cag cac tgc cag cgt cag tcc cag        3505
Leu Ala Val Tyr Leu Ser Cys Gln His Cys Gln Arg Gln Ser Gln
            1055                1060                1065 gag tcc aca ctg gtc cat cct gcc acc ccc aac cat ttg cac tac        3550
Glu Ser Thr Leu Val His Pro Ala Thr Pro Asn His Leu His Tyr
        1070                1075                1080 aag ggc gga ggc acc ccg aag aat gaa aag tac aca ccc atg gaa        3595
Lys Gly Gly Gly Thr Pro Lys Asn Glu Lys Tyr Thr Pro Met Glu
    1085                1090                1095 ttc aag acc ctg aac aag aat aac ttg atc cct gat gac aga gcc        3640
Phe Lys Thr Leu Asn Lys Asn Asn Leu Ile Pro Asp Asp Arg Ala
1100                1105                1110 aac ttc tac cca ttg cag cag acc aat gtg tac acg act act tac        3685
Asn Phe Tyr Pro Leu Gln Gln Thr Asn Val Tyr Thr Thr Thr Tyr
            1115                1120                1125 tac cca agc ccc ctg aac aaa cac agc ttc cgg ccc gag gcc tca        3730
Tyr Pro Ser Pro Leu Asn Lys His Ser Phe Arg Pro Glu Ala Ser
        1130                1135                1140 cct gga caa cgg tgc ttc ccc aac agc tga taccgccgtc ctggggactt      3780
Pro Gly Gln Arg Cys Phe Pro Asn Ser
    1145                1150 gggcttcttg ccttcataag gcacagagca gatggagatg ggacagtgga gccagtttgg    3840
```

```
ttttctccct ctgcactagg ccaagaactt gctgccttgc ctgtgggggg tcccatccgg    3900
cttcagagag ctctggctgg cattgaccat gggggaaagg gctggtttca ggctgacata    3960
tggccgcagg tccagttcag cccaggtctc tcatggttat cttccaaccc actgtcacgc    4020
tgacactatg ctgccatgcc tgggctgtgg acctactggg catttgagga attggagaat    4080
ggagatggca agagggcagg cttttaagtt tgggttggag acaacttcct gtggccccca    4140
caagctgagt ctggccttct ccagctggcc caaaaaagg cctttgctac atcctgatta    4200
tctctgaaag taatcaatca agtggctcca gtagctctgg attttctgcc agggctgggc    4260
cattgtggtg ctgccccagt atgacatggg accaaggcca gcgcaggtta tccacctctg    4320
cctggaagtc tatactctac ccagggcatc cctctggtca gaggcagtga gtactgggaa    4380
ctggaggctg acctgtgctt agaagtcctt taatctgggc tggtacaggc ctcagccttg    4440
ccctcaatgc acgaaaggtg cccaggaga gaggatcaat gccataggag cagaagtct    4500
ggcctctgtg cctctatgga gactatcttc cagttgctgc tcaacagagt tgttggctga    4560
gacctgcttg ggagtctctg ctggcccttc atctgttcag gaacacacac acacacacac    4620
tcacacacgc acacacaatc acaatttgct acagcaacaa aaaagacatt gggctgtggc    4680
attattaatt aaagatgata tccagtcaaa aaaaaaaaaa aaaaaaaaaa aaaaaaa      4737
```

```
<210> SEQ ID NO 49
<211> LENGTH: 1151
<212> TYPE: PRT
<213> ORGANISM: Homo sapiens

<400> SEQUENCE: 49

Met Pro Cys Gly Phe Ser Pro Ser Pro Val Ala His His Leu Val Pro
1               5                   10                  15

Gly Pro Pro Asp Thr Pro Ala Gln Gln Leu Arg Cys Gly Trp Thr Val
            20                  25                  30

Gly Gly Trp Leu Leu Ser Leu Val Arg Gly Leu Leu Pro Cys Leu Pro
        35                  40                  45

Pro Gly Ala Arg Thr Ala Glu Gly Pro Ile Met Val Leu Ala Gly Pro
    50                  55                  60

Leu Ala Val Ser Leu Leu Leu Pro Ser Leu Thr Leu Leu Val Ser His
65                  70                  75                  80

Leu Ser Ser Ser Gln Asp Val Ser Glu Pro Ser Ser Glu Gln Gln
                85                  90                  95

Leu Cys Ala Leu Ser Lys His Pro Thr Val Ala Phe Glu Asp Leu Gln
            100                 105                 110

Pro Trp Val Ser Asn Phe Thr Tyr Pro Gly Ala Arg Asp Phe Ser Gln
        115                 120                 125

Leu Ala Leu Asp Pro Ser Gly Asn Gln Leu Ile Val Gly Ala Arg Asn
    130                 135                 140

Tyr Leu Phe Arg Leu Ser Leu Ala Asn Val Ser Leu Leu Gln Ala Thr
145                 150                 155                 160

Glu Trp Ala Ser Ser Glu Asp Thr Arg Arg Ser Cys Gln Ser Lys Gly
                165                 170                 175

Lys Thr Glu Glu Glu Cys Gln Asn Tyr Val Arg Val Leu Ile Val Ala
            180                 185                 190

Gly Arg Lys Val Phe Met Cys Gly Thr Asn Ala Phe Ser Pro Met Cys
        195                 200                 205

Thr Ser Arg Gln Val Gly Asn Leu Ser Arg Thr Ile Glu Lys Ile Asn
```

-continued

Gly Val Ala Arg Cys Pro Tyr Asp Pro Arg His Asn Ser Thr Ala Val
225                 230                 235                 240

Ile Ser Ser Gln Gly Glu Leu Tyr Ala Ala Thr Val Ile Asp Phe Ser
            245                 250                 255

Gly Arg Asp Pro Ala Ile Tyr Arg Ser Leu Gly Ser Gly Pro Pro Leu
                260                 265                 270

Arg Thr Ala Gln Tyr Asn Ser Lys Trp Leu Asn Glu Pro Asn Phe Val
        275                 280                 285

Ala Ala Tyr Asp Ile Gly Leu Phe Ala Tyr Phe Leu Arg Glu Asn
    290                 295                 300

Ala Val Glu His Asp Cys Gly Arg Thr Val Tyr Ser Arg Val Ala Arg
305                 310                 315                 320

Val Cys Lys Asn Asp Val Gly Gly Arg Phe Leu Leu Glu Asp Thr Trp
                325                 330                 335

Thr Thr Phe Met Lys Ala Arg Leu Asn Cys Ser Arg Pro Gly Glu Val
                340                 345                 350

Pro Phe Tyr Tyr Asn Glu Leu Gln Ser Ala Phe His Leu Pro Glu Gln
        355                 360                 365

Asp Leu Ile Tyr Gly Val Phe Thr Thr Asn Val Asn Ser Ile Ala Ala
    370                 375                 380

Ser Ala Val Cys Ala Phe Asn Leu Ser Ala Ile Ser Gln Ala Phe Asn
385                 390                 395                 400

Gly Pro Phe Arg Tyr Gln Glu Asn Pro Arg Ala Ala Trp Leu Pro Ile
                405                 410                 415

Ala Asn Pro Ile Pro Asn Phe Gln Cys Gly Thr Leu Pro Glu Thr Gly
                420                 425                 430

Pro Asn Glu Asn Leu Thr Glu Arg Ser Leu Gln Asp Ala Gln Arg Leu
        435                 440                 445

Phe Leu Met Ser Glu Ala Val Gln Pro Val Thr Pro Glu Pro Cys Val
    450                 455                 460

Thr Gln Asp Ser Val Arg Phe Ser His Leu Val Val Asp Leu Val Gln
465                 470                 475                 480

Ala Lys Asp Thr Leu Tyr His Val Leu Tyr Ile Gly Thr Glu Ser Gly
                485                 490                 495

Thr Ile Leu Lys Ala Leu Ser Thr Ala Ser Arg Ser Leu His Gly Cys
                500                 505                 510

Tyr Leu Glu Glu Leu His Val Leu Pro Pro Gly Arg Arg Glu Pro Leu
        515                 520                 525

Arg Ser Leu Arg Ile Leu His Ser Ala Arg Ala Leu Phe Val Gly Leu
    530                 535                 540

Arg Asp Gly Val Leu Arg Val Pro Leu Glu Arg Cys Ala Ala Tyr Arg
545                 550                 555                 560

Ser Gln Gly Ala Cys Leu Gly Ala Arg Asp Pro Tyr Cys Gly Trp Asp
                565                 570                 575

Gly Lys Gln Gln Arg Cys Ser Thr Leu Glu Asp Ser Ser Asn Met Ser
            580                 585                 590

Leu Trp Thr Gln Asn Ile Thr Ala Cys Pro Val Arg Asn Val Thr Arg
        595                 600                 605

Asp Gly Gly Phe Gly Pro Trp Ser Pro Trp Gln Pro Cys Glu His Leu
    610                 615                 620

Asp Gly Asp Asn Ser Gly Ser Cys Leu Cys Arg Ala Arg Ser Cys Asp
625                 630                 635                 640

-continued

```
Ser Pro Arg Pro Arg Cys Gly Leu Asp Cys Leu Gly Pro Ala Ile
            645                 650                 655

His Ile Ala Asn Cys Ser Arg Asn Gly Ala Trp Thr Pro Trp Ser Ser
            660                 665                 670

Trp Ala Leu Cys Ser Thr Ser Cys Gly Ile Gly Phe Gln Val Arg Gln
            675                 680                 685

Arg Ser Cys Ser Asn Pro Ala Pro Arg His Gly Gly Arg Ile Cys Val
            690                 695                 700

Gly Lys Ser Arg Glu Glu Arg Phe Cys Asn Glu Asn Thr Pro Cys Pro
705                 710                 715                 720

Val Pro Ile Phe Trp Ala Ser Trp Gly Ser Trp Ser Lys Cys Ser Ser
                725                 730                 735

Asn Cys Gly Gly Gly Met Gln Ser Arg Arg Ala Cys Glu Asn Gly
            740                 745                 750

Asn Ser Cys Leu Gly Cys Gly Val Glu Phe Lys Thr Cys Asn Pro Glu
            755                 760                 765

Gly Cys Pro Glu Val Arg Arg Asn Thr Pro Trp Thr Pro Trp Leu Pro
            770                 775                 780

Val Asn Val Thr Gln Gly Gly Ala Arg Gln Gln Arg Phe Arg Phe
785                 790                 795                 800

Thr Cys Arg Ala Pro Leu Ala Asp Pro His Gly Leu Gln Phe Gly Arg
                805                 810                 815

Arg Arg Thr Glu Thr Arg Thr Cys Pro Ala Asp Gly Ser Gly Ser Cys
            820                 825                 830

Asp Thr Asp Ala Leu Val Glu Val Leu Leu Arg Ser Gly Ser Thr Ser
            835                 840                 845

Pro His Thr Val Ser Gly Gly Trp Ala Ala Trp Gly Pro Trp Ser Ser
            850                 855                 860

Cys Ser Arg Asp Cys Glu Leu Gly Phe Arg Val Arg Lys Arg Thr Cys
865                 870                 875                 880

Thr Asn Pro Glu Pro Arg Asn Gly Gly Leu Pro Cys Val Gly Asp Ala
                885                 890                 895

Ala Glu Tyr Gln Asp Cys Asn Pro Gln Ala Cys Pro Val Arg Gly Ala
            900                 905                 910

Trp Ser Cys Trp Thr Ser Trp Ser Pro Cys Ser Ala Ser Cys Gly Gly
            915                 920                 925

Gly His Tyr Gln Arg Thr Arg Ser Cys Thr Ser Pro Ala Pro Ser Pro
930                 935                 940

Gly Glu Asp Ile Cys Leu Gly Leu His Thr Glu Ala Leu Cys Ala
945                 950                 955                 960

Thr Gln Ala Cys Pro Glu Gly Trp Ser Pro Trp Ser Glu Trp Ser Lys
                965                 970                 975

Cys Thr Asp Asp Gly Ala Gln Ser Arg Ser Arg His Cys Glu Glu Leu
            980                 985                 990

Leu Pro Gly Ser Ser Ala Cys Ala  Gly Asn Ser Ser Gln  Ser Arg Pro
            995                 1000                1005

Cys Pro  Tyr Ser Glu Ile Pro  Val Ile Leu Pro Ala  Ser Ser Met
    1010                1015                1020

Glu Glu  Ala Thr Asp Cys Ala  Gly Phe Asn Leu Ile  His Leu Val
    1025                1030                1035

Ala Thr  Gly Ile Ser Cys Phe  Leu Gly Ser Gly Leu  Leu Thr Leu
    1040                1045                1050
```

```
Ala Val Tyr Leu Ser Cys Gln His Cys Gln Arg Gln Ser Gln Glu
    1055            1060                1065
Ser Thr Leu Val His Pro Ala Thr Pro Asn His Leu His Tyr Lys
    1070            1075                1080
Gly Gly Gly Thr Pro Lys Asn Glu Lys Tyr Thr Pro Met Glu Phe
    1085            1090                1095
Lys Thr Leu Asn Lys Asn Asn Leu Ile Pro Asp Asp Arg Ala Asn
    1100            1105                1110
Phe Tyr Pro Leu Gln Gln Thr Asn Val Tyr Thr Thr Thr Tyr Tyr
    1115            1120                1125
Pro Ser Pro Leu Asn Lys His Ser Phe Arg Pro Glu Ala Ser Pro
    1130            1135                1140
Gly Gln Arg Cys Phe Pro Asn Ser
    1145            1150

<210> SEQ ID NO 50
<211> LENGTH: 22
<212> TYPE: DNA
<213> ORGANISM: Artificial Sequence
<220> FEATURE:
<223> OTHER INFORMATION: A primer sequence

<400> SEQUENCE: 50
gtctaccagg cattcgcttc at                                            22

<210> SEQ ID NO 51
<211> LENGTH: 24
<212> TYPE: DNA
<213> ORGANISM: Artificial Sequence
<220> FEATURE:
<223> OTHER INFORMATION: a primer sequence

<400> SEQUENCE: 51
tcagctggac cacagccgca gcgt                                          24

<210> SEQ ID NO 52
<211> LENGTH: 21
<212> TYPE: DNA
<213> ORGANISM: Artificial Sequence
<220> FEATURE:
<223> OTHER INFORMATION: a primer sequence

<400> SEQUENCE: 52
tcagaaatcc tttctcttga c                                             21

<210> SEQ ID NO 53
<211> LENGTH: 24
<212> TYPE: DNA
<213> ORGANISM: Artificial Sequence
<220> FEATURE:
<223> OTHER INFORMATION: a primer sequence

<400> SEQUENCE: 53
ctagcctctg gaatcctttc tctt                                          24
```